(12) United States Patent
Akatsuka et al.

(10) Patent No.: US 6,383,353 B1
(45) Date of Patent: May 7, 2002

(54) OXYGEN SENSOR

(75) Inventors: Shoji Akatsuka; Satoshi Ishikawa; Masahiro Asai, all of Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/599,448

(22) Filed: Jun. 22, 2000

(30) Foreign Application Priority Data

Jun. 23, 1999 (JP) ............................................ 11-177469
Feb. 29, 2000 (JP) .......................................... 2000-54935

(51) Int. Cl.⁷ ............................................ G01N 27/407
(52) U.S. Cl. ........................ 204/424; 204/427; 204/428
(58) Field of Search ................................. 204/421–429

(56) References Cited

U.S. PATENT DOCUMENTS

| 4,741,816 A | 5/1988 | Nishio et al. |
| 5,679,226 A | * 10/1997 | Furusaki et al. |
| 5,759,365 A | 6/1998 | Yamada et al. |
| 5,804,050 A | 9/1998 | Hayakawa et al. |

\* cited by examiner

Primary Examiner—T. Tung
(74) Attorney, Agent, or Firm—Sughrue Mion, PLLC

(57) ABSTRACT

A sensor structure which reduces the resistance of insertion in the course of insertion of a metallic terminal member into the hollow portion of an oxygen detection element so as to enable smooth assembly and such that portions of the metallic terminal member become less susceptible to plastic deformation. An attachment portion 23c of a metallic terminal member 23 is in contact with the inner wall surface of a hollow portion 2a of an oxygen detection element 2, directly or indirectly via another member, at opposite sides thereof located along the direction of contact. Also, a gap is formed between an attachment portion 23c and the inner wall surface at opposite sides of the attachment portion 23c located along the direction of gap formation. Thus, in the course of insertion of the metallic terminal member 23 into the hollow portion 2a of the oxygen detection element 2, the resistance of insertion decreases, whereby assembly can be performed smoothly, and portions of the metallic terminal member 23 become less susceptible to plastic deformation, such as crushing, bending, or buckling.

17 Claims, 17 Drawing Sheets

Fig. 9 (a)
Fig. 9 (b)
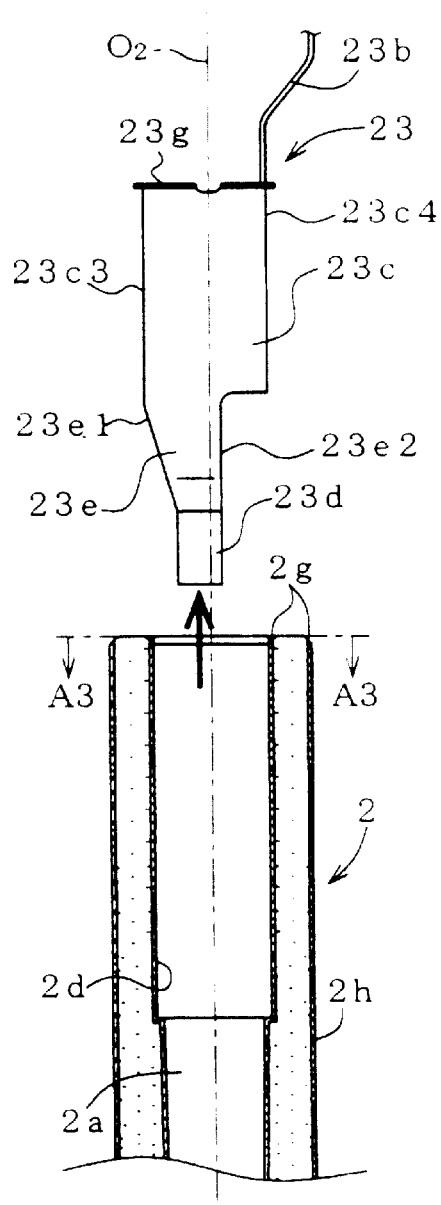
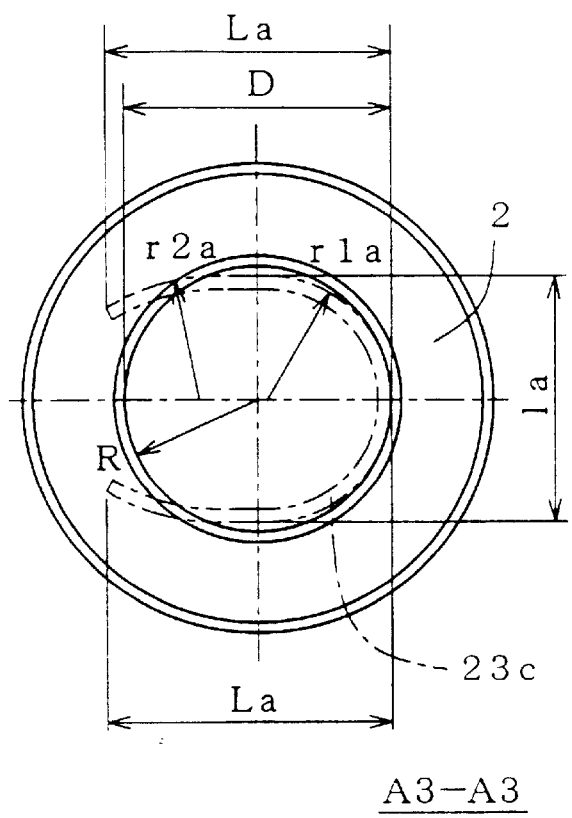
A3–A3

| No. | 1 | 2 | 3 | 4 | 5 |
|---|---|---|---|---|---|
| DEVELOPMENT (ESSENTIAL PORTION) | | | | | |
| REDUCTION PORTION 23h3 | ABSENT | SEMICIRCLE | SEMICIRCLE | INVERTED LETTER V | INVERTED LETTER V |
| SUB-CUT PORTION 23hi | ABSENT | ABSENT | SLIT | SLIT | GROOVE |
| FRONT VIEW (ESSENTIAL PORTION) | | | | | |

OXYGEN SENSOR

BACKGROUND OF THE INVENTION

1. Field of the Invention

The present invention relates to an oxygen sensor for detecting oxygen in a gas to be measured, such as exhaust gas from an internal combustion engine.

2. Description of the Related Art

A known oxygen sensor includes an oxygen detection element assuming the form of a hollow rod which is closed at a front end, and having electrode layers formed on the inner and outer surfaces thereof. In an oxygen sensor of this type, while the atmosphere serving as a reference gas is introduced into an oxygen detection element such that the inner surface (internal electrode layer) of the element is exposed to the reference gas, the outer surface (external electrode layer) of the oxygen detection element is exposed to exhaust gas. As a result, an electromotive force is induced by the oxygen concentration cell effect, according to the difference in oxygen concentration between the inner and outer surfaces. This electromotive force induced by the oxygen concentration cell effect is led out from the internal and external electrode layers through lead wires and serves as a detection signal indicative of oxygen concentration in the exhaust gas.

FIG. 12 of the accompanying drawings shows a conventional metallic internal-electrode connection member (metallic terminal member) 23' to be installed into a hollow portion 2a of such an oxygen detection element 2 so as to establish electrical connection with an internal electrode layer formed on the inner wall surface of the hollow portion 2a. The conventional metallic internal-electrode connection member 23' includes the following integrally formed portions: a connector 23a' to be connected to a lead wire; a main body portion 23c' to come into contact with the inner wall surface of the hollow portion 2a of the oxygen detection element 2; a lead portion 23b' for connecting the connector 23a' and the main body portion 23c'; and a heating member holder portion 23d' for firmly holding a heating member which is disposed within the hollow portion 2a for heating the oxygen detection element 2.

The main body portion 23c' of the conventional metallic internal-electrode connection member 23' is formed by bending into a cylindrical form a sheet member which has a plurality of contact portions 23e' formed into a saw-toothed form and arranged at opposite side edges thereof in a staggered manner. Substantially the entire outer circumferential surface of the main body portion 23c' is brought into contact with the inner wall surface (internal electrode layer) of the hollow portion 2a of the oxygen detection element 2, whereby electrical continuity is established and the main body portion 23c' is axially positioned relative to the hollow portion 2a.

In order to reliably position the metallic internal-electrode connection member 23' in the axial direction relative to the hollow portion 2a and to establish reliable contact and electrical connection between the metallic internal-electrode connection member 23' and the internal electrode layer, the outside diameter of the cylindrical main body portion 23c' is rendered greater than the inside diameter of the hollow portion 2a of the oxygen detection element 2a. Thus, as shown in FIG. 12, when the metallic internal-electrode connection member 23' is to be installed in the oxygen detection element 2, the main body portion 23c' is inserted under pressure into the hollow portion 2a while substantially the entire outer circumferential surface of the main body portion 23c' is squeezed radially. As a result, the resistance of insertion tends to increase, potentially raising a problem in assembly. Particularly, since a plurality of contact portions 23e' formed into a saw-toothed form are arranged at opposite sides in a staggered manner, the resistance of insertion tends to occur intermittently. As a result, in some cases, an upper portion (the base-end side relative to the insertion direction) of the metallic internal-electrode connection member 23' suffers plastic deformation, such as crushing, bending, or buckling. In order to prevent such plastic deformation, a relevant jig may be employed; however, this involves additional work and causes an increase in cost.

SUMMARY OF THE INVENTION

It is an object of the present invention to provide a sensor structure which reduces the resistance of insertion in the course of insertion of a metallic terminal member into the hollow portion of an oxygen detection element so as to enable smooth assembly, and such that portions of the metallic terminal member become less susceptible to plastic deformation.

Accordingly, an oxygen sensor of the present invention comprises an oxygen detection element assuming the form of a hollow rod which is closed at one end, and having an electrode layer formed on at least the inner surface thereof; and a metallic terminal member connected electrically to the electrode layer. The oxygen sensor is characterized in that:

the metallic terminal member includes an attachment portion having a substantially circular cross section, which is disposed within a hollow portion of the oxygen detection element; and the attachment portion is disposed such that, as observed in cross section, the attachment portion is in contact with the inner wall surface of the hollow portion of the oxygen detection element at opposite sides thereof located along a predetermined direction (hereinafter called the direction of contact), and a gap is formed between the attachment portion and the inner wall surface of the hollow portion of the oxygen detection element at opposite sides thereof located along a direction intersecting the direction of contact (hereinafter called the direction of gap formation).

As described above, according to the present invention, the attachment portion of the metallic terminal member is in contact with the inner wall surface of the hollow portion of the oxygen detection element, directly or indirectly via another member, at opposite sides thereof located along the direction of contact. Also, a gap is formed between the attachment portion and the inner wall surface at opposite sides of the attachment portion located along the direction of gap formation. Thus, only a portion of the outer circumferential surface of the attachment portion is in contact with the inner wall surface of the hollow portion to thereby establish electrical continuity therebetween. Specifically, the attachment portion is in contact with the inner wall surface of the hollow portion at two or more contact points to thereby establish electrical continuity therebetween. Thus, in the course of insertion of the metallic terminal member into the hollow portion of the oxygen detection element, the resistance of insertion decreases, whereby assembly can be performed smoothly, and portions of the metallic terminal member become less susceptible to plastic deformation, such as crushing, bending, or buckling.

Preferably, the attachment portion of the present invention, as observed in cross section, has an opening formed at a portion of the circumference thereof and includes a direction change portion, which is located opposite the opening with respect to the center axis of the hollow portion of the oxygen detection element; and edge portions located at opposite sides of the opening and the direction change portion are in contact with the inner wall surface of the hollow portion of the oxygen detection element, directly or indirectly via another member, and a direction extending between the direction change portion and one of the edge portions located at opposite sides of the opening is the direction of contact. Thus, the attachment portion can be manufactured through bending of a sheet member. Also, the attachment portion can be designed and machined with high accuracy so as to establish the above-mentioned state of contact and gap formation. By virtue of the opening, the attachment portion is inserted under pressure into the hollow portion while being elastically deformed such that the edge portions located at opposite sides of the opening are squeezed radially inward, whereby insertion is performed smoothly. Further, the attachment portion is in contact with the inner wall surface of the hollow portion of the oxygen detection element at the three portions-edge portions located at opposite sides of the opening, and the direction change portion—to thereby be fixedly positioned in a stable manner.

Preferably, the attachment portion of the present invention, as observed in cross section, includes parallel portions which are located opposite each other along the direction of gap formation. Thus, in the course of design and machining, the state of gap formation can be established easily and reliably, thereby facilitating installation.

Preferably, the attachment portion of the present invention is inserted in the hollow portion of the oxygen detection element in such manner as to be elastically deformed radially inward; and when the attachment portion is removed from the hollow portion while being elastically restored, as observed in cross section, a maximum distance between opposite points of the attachment portion located along the direction of contact and as projected on a line passing through the center of width of the opening and the center of the hollow portion is equal to or greater than the inside diameter of the oxygen detection element. By virtue of a resilient force associated with squeezing of the engagement portion in the direction of contact, the attachment portion is brought into reliable and secure contact with the inner wall surface of the hollow portion of the oxygen detection element, directly or indirectly via another member.

Preferably, according to the present invention, as observed in a longitudinal section which includes the opening and the center axis of the metallic terminal member, the edge portions located at opposite sides of the opening extend linearly in the direction of the axis of the hollow portion of the oxygen detection element. In contrast with the conventional type in which a plurality of contact portions formed into a saw-toothed form are arranged at opposite sides in a staggered manner with resultant intermittent occurrence of the resistance of insertion, the resistance of insertion is reduced, thereby enabling further smooth insertion of the metallic terminal member.

Preferably, according to the present invention, a diameter reduction portion is formed on the attachment portion at the front side relative to the insertion direction of the attachment portion into the hollow portion of the oxygen detection element; and, as observed in the longitudinal section which includes the opening and the center axis of the metallic terminal member, the diameter reduction portion includes a portion (hereinafter called a first portion) which is located adjacent to the edge portions located at opposite sides of the opening and which decreases in diameter continuously or stepwise at the front-end side relative to the insertion direction. The metallic terminal member is inserted into the hollow portion of the oxygen detection element while the first portion is guided by the hollow portion, and insertion of the edge portions located at opposite sides of the opening follows insertion of the first portion. Thus, the resistance of insertion in the course of assembly is further reduced, and the inserted metallic terminal member is in reliable and secure contact with the inner wall surface of the hollow portion.

Preferably, according to the present invention, at a contact portion between the attachment portion of the metallic terminal member and the inner wall surface of the hollow portion of the oxygen detection element, the radius of curvature of the outer circumferential surface of the attachment portion is smaller than that of the inner wall surface. Thus, the area of contact at the contact portion is reduced, thereby reducing the resistance of insertion of the attachment portion in the course of assembly.

Preferably, according to the present invention, a counterbore portion is formed in a rear-end opening portion of the hollow portion of the oxygen detection in a diameter-expanded manner so as to receive the attachment portion, directly or indirectly via another member. This structure prevents plastic deformation of the attachment portion, which would otherwise occur in association with insertion into the hollow portion of the oxygen detection element, and play or coming-off of the attachment portion, which would otherwise occur due to exposure to repeated vibration. Thus, the metallic terminal member can be fixedly positioned within the oxygen detection element in a smooth and reliable manner.

Preferably, the diameter reduction portion may include a portion (hereinafter called a second portion) which is located opposite the first portion with respect to the center axis of the hollow portion of the oxygen detection element and which, as observed in the longitudinal section which includes the opening and the center axis of the metallic terminal member, decreases in size continuously or stepwise toward the front-end side relative to the insertion direction. In the course of insertion of the metallic terminal member into the hollow portion of the oxygen detection element, the second portion contributes to further reduction in the resistance of insertion of the diameter reduction portion and to reliable, secure attachment of the metallic terminal member onto the inner wall surface of the hollow portion.

Preferably, the second portion of the diameter reduction portion may have a cut formed therein extending from the front end thereof relative to the insertion direction toward the base-end side relative to the insertion direction. The cut formed in the second portion contributes to a great reduction in the resistance of insertion of the attachment portion, particularly at the beginning of insertion. A reduction portion may be formed at the bottom of the cut such that the width along the circumferential direction of the inner wall surface of the hollow portion of the oxygen detection element decreases continuously toward the base-end side relative to the insertion direction. The reduction portion formed at the bottom of the cut contributes to a great reduction in the resistance of insertion, particularly at the end position of the diameter reduction portion in the course of insertion of insertion.

Preferably, the outline of the cut in the present invention as projected on a longitudinal section which includes the bottom point of the cut and the center axis of the metallic terminal member may assume a form so as to approach the inner wall surface of the hollow portion toward the base-end side relative to the insertion direction. The outline assuming this form may be realized by, for example, formation of a sub-cut in the second portion in such manner as to extend from the bottom of the cut toward the base-end side relative to the insertion direction. In any case, since the outline assumes such a form as to gradually approach the inner wall surface of the hollow portion toward the base-end side relative to the insertion direction, the second portion is rounded at the base-end side thereof relative to the insertion direction, and the rounded portion comes into contact with the inner wall surface of the hollow portion, thereby further reducing the resistance of insertion of the diameter reduction portion in the course of assembly. Also, chipping of the electrode layer becomes less likely to occur.

As a result of forming the sub-cut in the second portion, the outline of the cut includes an inflection point at which the form of a radially inward convex at the front-end side thereof relative to the insertion direction changes to the form of a radially outward convex at the base-end side thereof relative to the insertion direction. The outline may include a region in which the rate of change gradually decreases toward the inner wall surface of the hollow portion, where the rate of change is represented by a fraction having a denominator indicative of the amount of change in the direction of insertion and a numerator indicative of the amount of change in a radially outward direction perpendicular to the direction of insertion.

By forming the sub-cut in the second portion of the diameter reduction portion as mentioned above, the outline of the cut includes an inflection point, whereby the outline of the cut includes a rate-of-change gradual-decrease region. By forming the rate-of-change gradual-decrease region, at the base-end side of the second portion relative to the insertion direction, the amount of approach in a radially outward direction (the amount of approach to the inner wall surface of the hollow portion of the oxygen detection element) decreases gradually as the amount of insertion of the diameter reduction portion increases. Thus, in the course of assembly, the resistance of insertion of the diameter reduction portion further decreases. Also, while the second portion maintains a smooth outline, the rate of dimensional change in the axial direction (the direction of insertion) can be rendered great as compared to the rate of dimensional change in a radial direction. Thus, the size of the metallic terminal member can be reduced, whereby the oxygen detection element and the oxygen sensor can be formed to a compact size.

BRIEF DESCRIPTION OF THE DRAWINGS

FIGS. 9(a) and 9(b) show a front view and a plan view for explaining removal of the metallic internal-electrode connection member from the oxygen detection element.

FIG. 17 is a schematic front view and development showing the forms of metallic internal-electrode connection members for test use.

Figure 1:
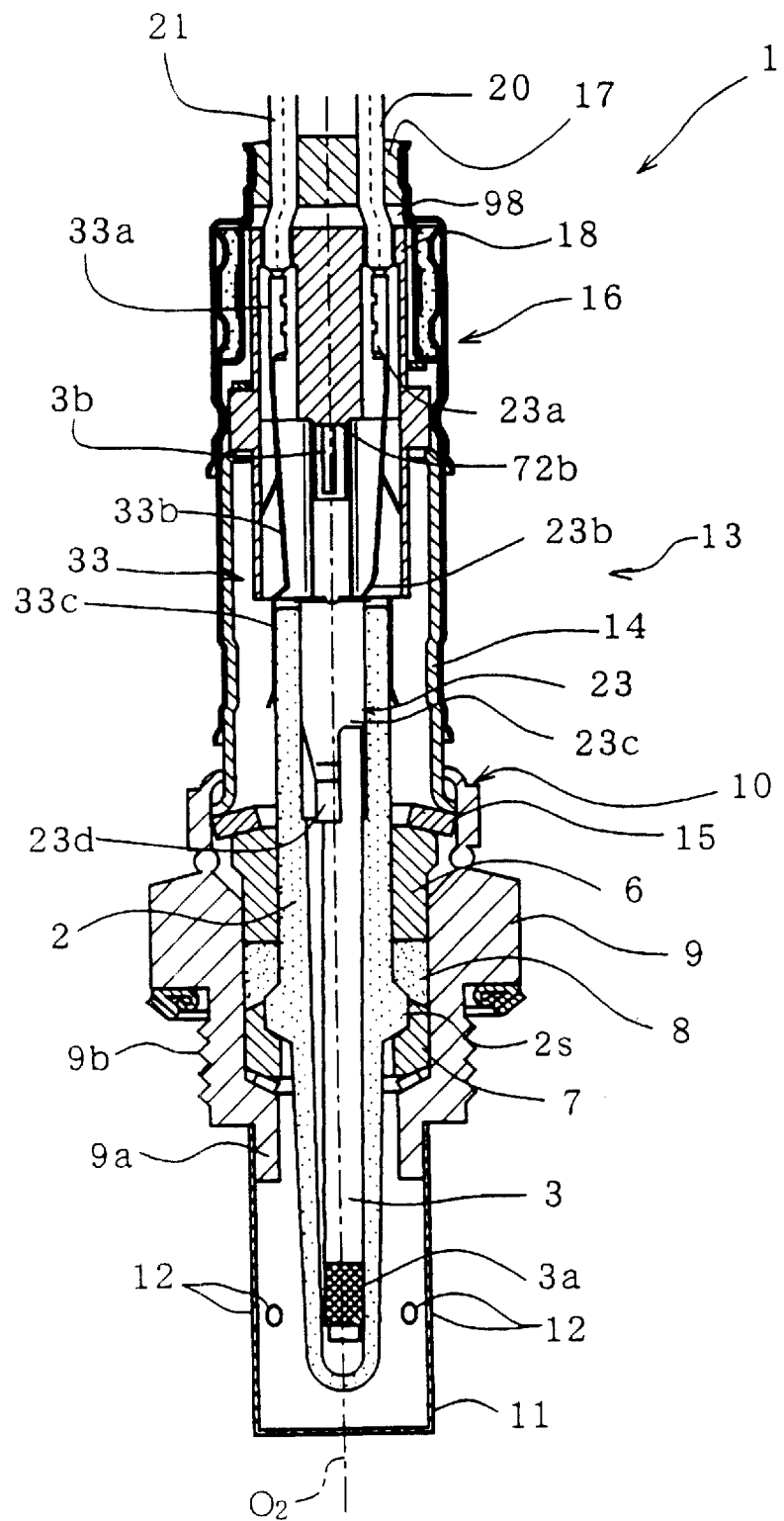
FIG. 1 is a longitudinal sectional view of an oxygen sensor of the present invention.

Reference numerals are used in the drawings to identify items as follows:
1: oxygen sensor
2: oxygen detection element
2a: hollow portion
2b: external electrode layer
2c: internal electrode layer (electrode layer)
2d: counter-bore (counter-bore portion)
23: metallic internal-electrode connection member (metallic terminal member)
23c: engagement portion (attachment portion)
23c1: opening
23c2: parallel portions
23c3: edge portions located at opposite sides of opening (contact portions)
23c4: direction change portion (contact portion)
23e: diameter reduction portion
23e1: first portion
23e2: second portion
23h: cut
23h1: opening of cut
23h2: bottom of cut
23h3: reduction portion
23i: sub-cut D: inside diameter of oxygen detection element La: in a state of removal of a metallic internal-electrode connection member and as observed in cross section, distance between opposite points of an engagement portion located along the direction of contact and as projected on the line passing through the center of the width of an opening and the center of a hollow portion (radial dimension after removal)

R: radius of curvature of inner wall surface of oxygen detection element r': radius of curvature of outer circumferential surface of engagement portion as measured after insertion K: cut line G: outline $O_2$: center axis of hollow portion of oxygen detection element P: inflection point S: gap

DESCRIPTION OF THE PREFERRED EMBODIMENTS

The present invention will now be explained by reference to the drawings. However, the present invention should not be construed as being limited thereto.

Figure 2:
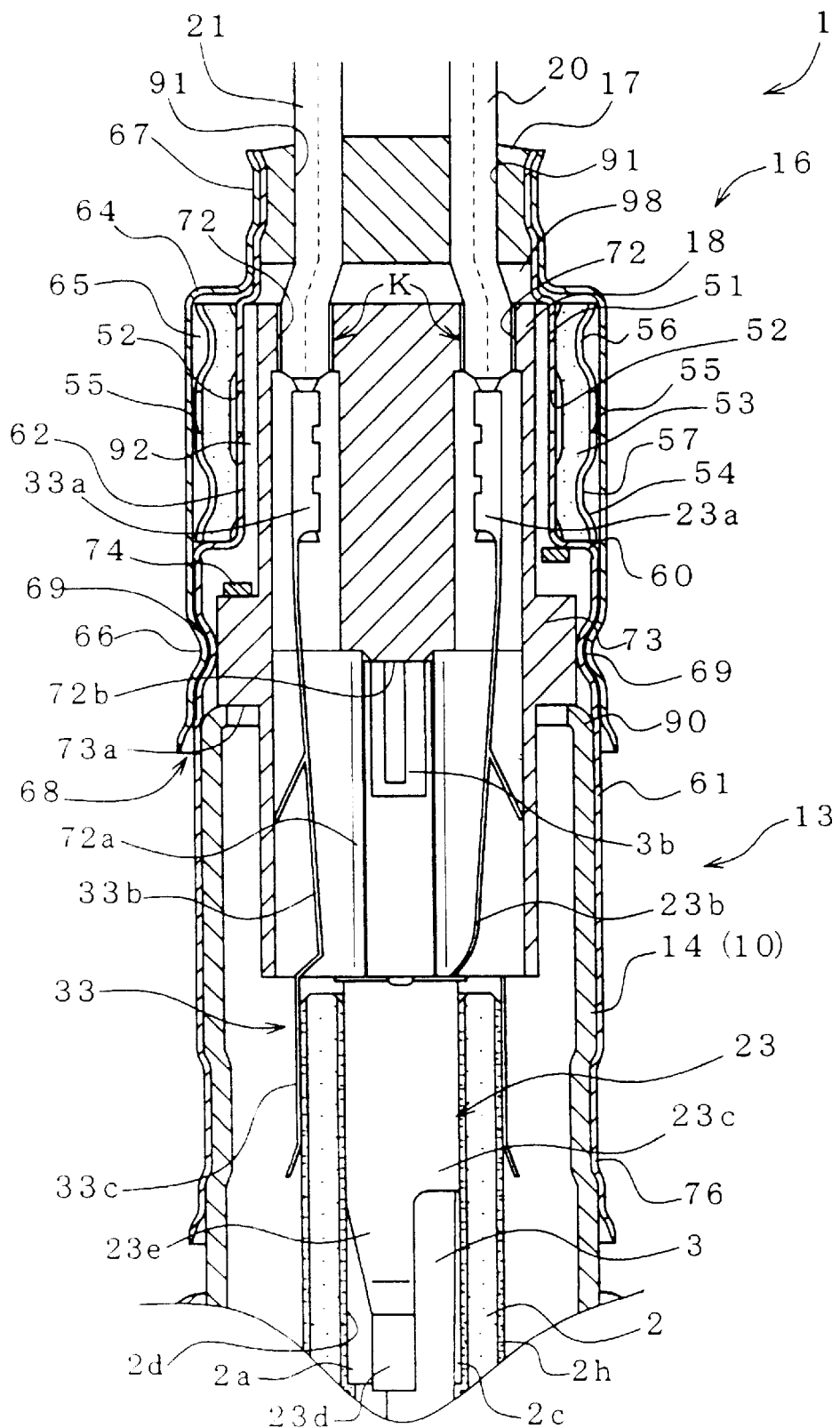
FIG. 2 is a partially enlarged longitudinal sectional view of the oxygen sensor of FIG. 1.

FIG. 1 shows the internal structure of an oxygen sensor of the present invention. FIG. 2 is an enlarged view of a main portion of the oxygen sensor. An oxygen sensor 1 includes an oxygen detection element 2, which is a solid electrolyte member assuming the form of a hollow rod which is closed at a front end, and a heating member 3 inserted into a hollow portion 2a of the oxygen detection element 2. The oxygen detection element 2 is formed into a hollow form from an oxygen-ion-conductive solid electrolyte. A typical example of such a solid electrolyte of $ZrO_2$ containing $Y_2O_3$ or CaO. Alternatively, a solid solution of $ZrO_2$ containing an oxide of an alkaline earth metal or a rare earth metal may be used. $ZrO_2$ serving as a base material may contain $HfO_2$. A metallic casing 10 is disposed to surround an intermediate portion of the oxygen detection element 2; and insulators 6 and 7 of insulating ceramic and a ceramic powder 8 of talc are disposed between the metallic casing 10 and the intermediate portion of the oxygen detection element 2. In the following description, the term "front side" or the like refers to the side of a front end portion (closed end portion) of the oxygen detection element 2, whereas the term "rear side" or the like refers to the side opposite the "front side."

Figure 4:
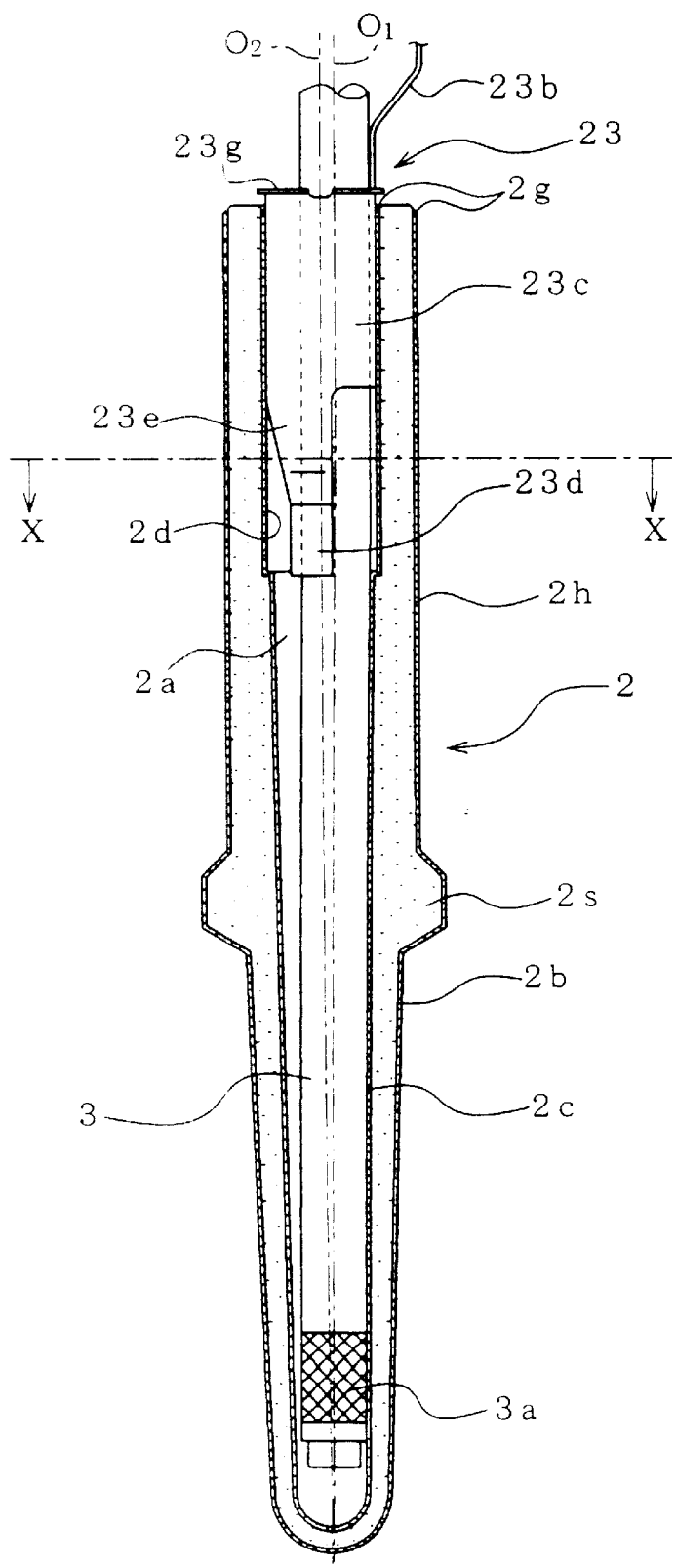
FIG. 4 is a longitudinal sectional view showing installation of the metallic internal-electrode connection member and the heating member into the oxygen detection element.

The casing 10 includes a metallic shell 9 having a threaded portion 9b. The threaded portion 9b is engaged with a mounting portion of, for example, an exhaust pipe, thereby attaching the oxygen sensor 1 to the exhaust pipe. A main cylindrical member 14 is connected to a rear-side opening portion of the metallic shell 9 in such a manner as to establish internal communication. A protector 11 is attached to a front-side opening portion of the metallic shell 9 so as to cover a front-side end portion (detection portion) of the oxygen detection element 2. A portion of the oxygen sensor 1 which is located on the front side of the threaded portion 9b is located within a system of an engine, such as within an exhaust pipe, whereas the remaining rear-side portion is located in the exterior atmosphere. As shown in FIGS. 2 and 4, an internal electrode layer 2c is formed on substantially the entire inner surface of the hollow portion 2a, whereas an external electrode layer 2b is formed on the outer surface of the hollow portion 2a in such a manner as to cover a front portion of the outer surface. The internal and external electrode layers 2c and 2b are porous and formed from, for example, Pt or a Pt alloy.

The main cylindrical member 14 is caulked to the rear-side opening portion of the metallic shell 9 while a ring 15 is interposed between the main cylindrical member 14 and the insulator 6. A cylindrical filter assembly 16 is fixedly fitted onto the main cylindrical member 14. A ceramic separator 18 is disposed at the rear side of the oxygen detection element 2 substantially coaxial with the casing 10. A plurality of lead wire through-holes 72 are formed axially in the ceramic separator 18. Lead wires 20 and 21 for the oxygen detection element 2 and lead wires (not shown) for the heating member 3 extend through the corresponding lead wire through-holes 72. A heating-member-end-portion accommodation hole 72a is formed in the ceramic separator 18 so as to extend axially there into from the front end face thereof. The inside diameter of the heating-member-end-portion accommodation hole 72a is greater than the outside diameter of the heating member 3. A bottom surface 72b of the heating-member-end-portion accommodation hole 72a is located at an axially intermediate portion of the ceramic separator 18.

The filter assembly 16 assumes a cylindrical form and is substantially coaxially connected to the main cylindrical member 14 (casing 10) from the rear side. The filter assembly 16 includes a first filter holder 51 having a plurality of gas inlet holes 52 formed in a wall portion thereof. A cylindrical filter 53 (a water-repellent resin filter formed from, for example, a porous material of polytetrafluoroethylene) is disposed outside the first filter holder 51 so as to block the gas inlet holes 52. A second filter holder 54-which has one or more gas inlet holes 55 formed in a wall portion thereof-is disposed outside the filter 53 to thereby hold the filter 53 in cooperation with the first filter holder 51. A grommet 17 of rubber is elastically fitted into a rear-end opening portion of the first filter holder 51. A plurality of lead wire through-holes 91 are formed axially in the grommet 17 for allowing the lead wires 20 and 21 to extend therethrough. Thus, the grommet 17 fills the space between the external surfaces of the lead wires 20, 21, etc. and the inner surface of an opening portion of the first filter holder 51 for the purpose of forming a seal. Notably, in the present embodiment, the filter assembly 16 is fixedly attached to the main cylindrical member 14, thereby forming an external cylindrical member 13. However, the external cylindrical member 13 may assume a simple structure without employment of a filter assembly. In the case of the external cylindrical member 13 that does not employ a filter assembly, a separate airing portion may be formed for the grommet 17.

The lead wire 20 for the oxygen detection element 2 is electrically connected to the internal electrode layer 2c (FIG. 2) of the oxygen detection element 2 through a metallic internal-electrode connection member 23 (metallic terminal member). The internal electrode connector 23 includes the following integrally formed portions: a connector 23a, a lead portion 23b, an engagement portion 23c (attachment portion), and a press portion 23d. The other lead wire 21 is electrically connected to the external electrode layer 2b (FIG. 2) through a metallic external-electrode connection member 33. The metallic external-electrode connection member 33 includes the following integrally formed portions: a connector 33a, a lead portion 33b, and a main body portion 33c. The oxygen detection element 2 is heated by the heating member 3 disposed within the same to thereby activate the sensor. The heating member 3 is a rodlike ceramic heater and includes a core member which contains a predominant amount of $Al_2O_3$, a heating portion 3a having a heating resistor (not shown), and two heating-member terminal portions 3b. The heating member 3 is electrically energized through lead wires (not shown) connected to the heating-member terminal portion 3b on the positive-pole side and the heating-member terminal portion 3b on the negative-pole side to thereby heat the oxygen detection element 2.

Figure 3:
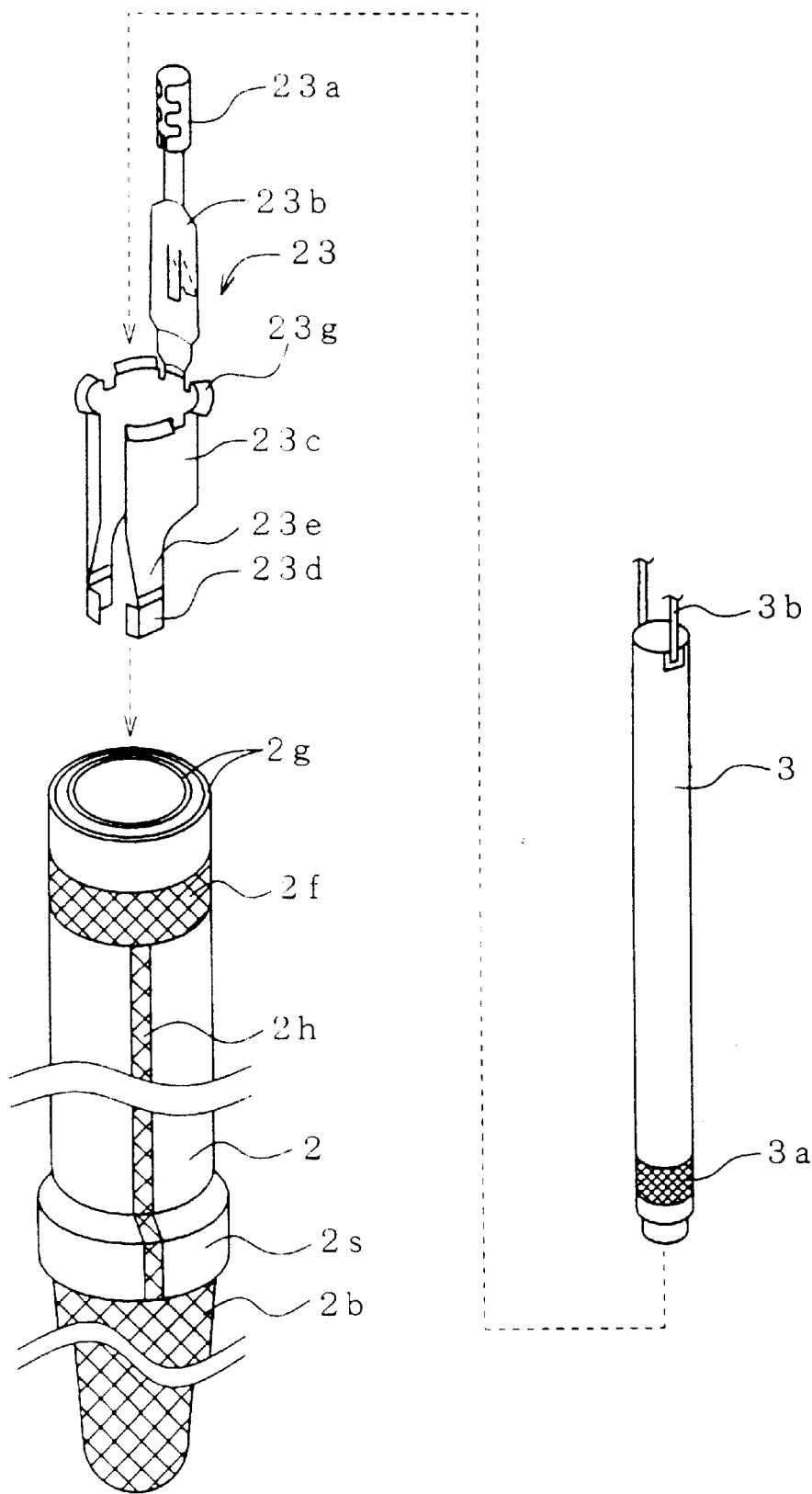
FIG. 3 is an exploded perspective view showing installation of a metallic internal-electrode connection member and a heating member into an oxygen detection element.

As shown in FIGS. 3 and 4, the heating member 3 is inserted into the metallic internal-electrode connection member 23 (metallic terminal member) from the rear side. The external circumferential surface of the heating member 3 is brought into contact with the inner surface of the press portion 23d, which is formed at the front-end side of the metallic internal-electrode connection member 23. As a result, the press portion 23d presses the heating member 3 in a direction intersecting a center axis $O_2$ of the hollow portion 2a of the oxygen detection element 2, thereby bringing at least a portion of the heating member 3 into contact with the inner wall surface of the hollow portion 2a of the oxygen detection element 2. The outer surface of the engagement portion 23c adjacent to the press portion 23d is fitted into the hollow portion 2a of the oxygen detection element 2, thereby fixedly positioning the metallic internal-electrode connection member 23 in the axial direction of the oxygen detection element 2. One end of the lead portion 23b is integrally connected to the engagement portion 23c at a circumferential position. The other end of the lead portion 23b is integrated with the connector 23a. Reference numeral 23g denotes a flange for preventing the engagement portion 23c from entering too far into the heating-member-end-portion accommodation hole 72a.

The press portion 23d is composed of two bent members which each have a substantially L-shaped cross section and face each other so as to surround the heating member 3. When the heating member 3 is inserted into the engagement portion 23c, the press portion 23d is elastically widened from inside. The resulting elastic restoration force; i.e., a pressing force, presses the heating member 3 in a direction intersecting the center axis $O_2$ of the hollow portion 2a of the oxygen detection element 2.

The engagement portion 23c (attachment portion) is formed into a circumferentially open-ended form by bending of a sheet segment to thereby form an opening, and includes a direction change portion, which is located opposite the opening with respect to the center axis $O_2$ of the hollow portion 2a of the oxygen detection element 2, thereby assuming a horseshoe-like cross section taken perpendicularly to the axis. A portion of the outer circumferential surface of the engagement portion 23c is in contact with the inner wall surface of the hollow portion 2a of the oxygen detection element 2, whereby the metallic internal-electrode connection member 23 is fixedly positioned in the axial direction of the oxygen detection element 2 and is electrically connected to the internal electrode layer 2c.

A counter-bore 2d (counter-bore portion) is formed in the hollow portion 2a of the oxygen detection element 2 so as to extend axially from the end face of a rear-end opening portion of the oxygen detection element 2 longer than the axial engagement length of the engagement portion 23c. The engagement portion 23c is directly inserted into the counter-bore 2d. The counter-bore 2d is formed by boring of the hollow portion 2a such that the axis thereof coincides with the center axis $O_2$ of the hollow portion 2a of the oxygen detection element 2 and in such a diameter-expanded manner that the diameter thereof is equal to or slightly greater than the maximum inside diameter (the inside diameter of a rear-end opening portion) of the hollow portion 2a. Thus, the metallic internal-electrode connection member 23 can be fixedly situated within the oxygen detection element 2 in a smooth and reliable manner. By forming a chamfer 2g at an internal edge of the rear-end opening portion of the hollow portion 2a of the oxygen detection element 2, the metallic internal-electrode connection member 23 can be smoothly fitted into the oxygen detection element 2 without incurring a defect, such as chipping, of the oxygen detection element 2. A portion of the outer circumferential surface of the engagement portion 23c may be electrically connected to the internal electrode layer 2c through contact via another member with the inner wall surface of the hollow portion 2a (wall surface of the counter-bore 2d) of the oxygen detection element 2. The diameter of the hollow portion 2a is comparatively larger at its opening and narrower at its bottom as a result of forming and sintering the oxygen detection element ceramic.

Referring back to FIG. 2, the metallic external-electrode connection member 33 includes the cylindrical main body portion 33c. One end of the lead portion 33b is integrally connected to the main body portion 33c at a circumferential position. The other end of the lead portion 33b is integrated with the connector 33a. A rear-end portion of the oxygen detection element 2 is inserted into the main body portion 33c so as to elastically widen the main body portion 33c from inside. As shown in FIG. 3, a conductive layer 2f assuming the shape of a circumferentially extending strip is formed on the outer surface of a rear-end portion of the oxygen detection element 2 and serves as an output terminal portion for output to the exterior of the oxygen sensor. The external electrode layer 2b is formed on the oxygen detection element 2 so as to cover the entire surface of an essential portion of the oxygen detection element 2 located on the front-end side with respect to an engagement flange portion 2s, which is formed at a substantially intermediate portion of the oxygen detection element 2. The conductive layer 2f and the external electrode layer 2b are electrically connected through a linear connection pattern layer 2h.

In the oxygen sensor 1, the atmosphere serving as a reference gas is introduced to the inner surface (internal electrode layer 2c) of the oxygen detection element 2 along the following route: a port 68 for communication with the ambient atmosphere→a groove portion 69→a gas detention space 65→a gas inlet port 55→the filter 53→a gas inlet port 52→a gap 92→a gap 98→a gap K→the hollow portion 2a. An exhaust gas is introduced through gas transmission holes 12 formed in the protector 11 and comes into contact with the outer surface (external electrode layer 2b) of the oxygen detection element 2. As a result, an electromotive force is generated in the oxygen detection element 2 by the oxygen concentration cell effect, according to the difference in oxygen concentration between the inner and outer surfaces. The thus-generated electromotive force is output in the form of a detection signal indicative of oxygen concentration in the exhaust gas. The signal is output from the internal and external electrode layers 2c and 2b (FIG. 2) through the metallic connection members 23 and 33 and lead wires 20 and 21, thereby detecting oxygen concentration in the exhaust gas.

Referring to FIG. 4, the positional relationship between the center axis $O_1$ of the heating member 3 and the center axis $O_2$ of the hollow portion 2a of the oxygen detection element 2 is represented in the following manner. In the oxygen sensor of the present embodiment, the center axis $O_1$ of the heating member 3 approaches the center axis $O_2$ of the hollow portion 2a of the oxygen detection element 2 toward the front side. This results from the press portion 23d pressing the metallic internal-electrode connection member 23 in a direction intersecting the center axis $O_2$ of the hollow portion 2a of the oxygen detection element 2. As a result, the center axis $O_1$ of the heating member 3 is laterally biased (offset) from the center axis $O_2$ of the hollow portion 2a of the oxygen detection element 2. The positional relationship between the surface of the heating portion 3a of the heating member 3 and the inner wall surface of the hollow portion 2a of the oxygen detection element 2 is represented in the following manner. In a so-called lateral abutment feature, in which the surface of the heating portion 3a of the heating member 3 is laterally pressed against the inner wall surface of the hollow portion 2a of the oxygen detection element 2, a state (so-called overall contact state) in which the surface of the heating member 3 is in contact with the inner wall surface of the hollow portion 2a of the oxygen detection element 2 over substantially the entire length of the heating member 3 is established. By employing the lateral abutment feature, heat generated by the heating member 3 is efficiently transmitted to the oxygen detection element 2, thereby improving activation of startup of the oxygen detection element 2.

In the actual overall contact state, the entire surface of the heating member 3 is not in contact with the inner wall surface of the hollow portion 2a of the oxygen detection element 2, but the above-mentioned designation is used for convenience. The inner wall surface of the hollow portion 2a of the oxygen detection element 2 is slightly tapered in the course of manufacture such that the diameter reduces toward a bottom portion. In the overall contact state shown in FIG. 4, the inclination angle of the center axis $O_1$ of the heating member 3 to the center axis $O_2$ of the hollow portion 2a of the oxygen detection element 2 substantially coincides with this taper.

Figure 5:
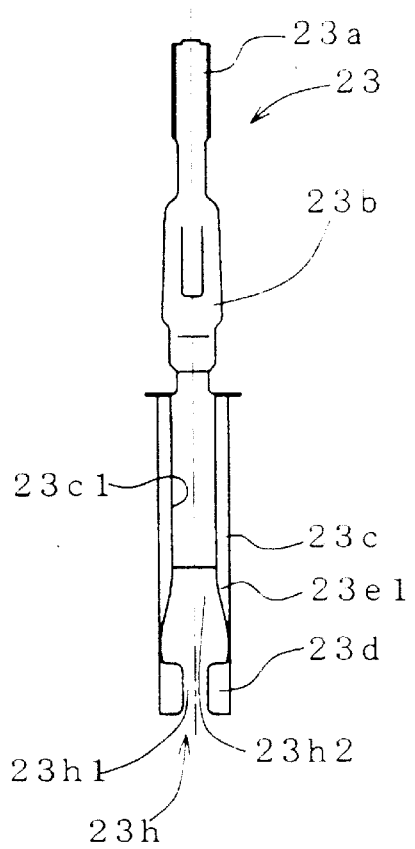
FIGS. 5(a), 5(b) and 5(c) show a left-hand side view, front view, and development of a metallic internal-electrode connection member, respectively.
Figure 5:
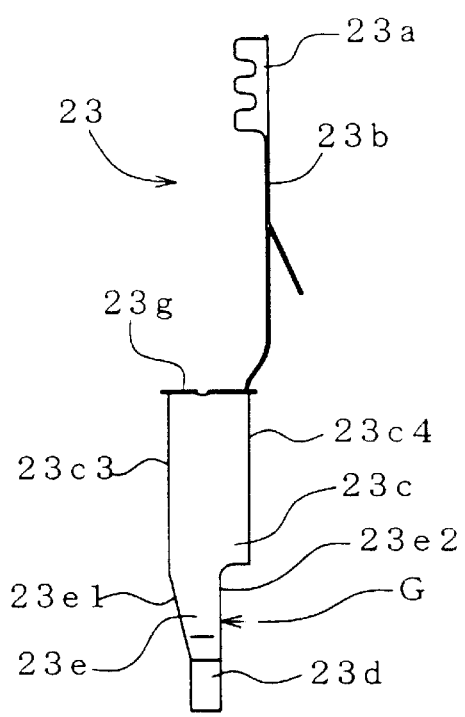
Figure 5:
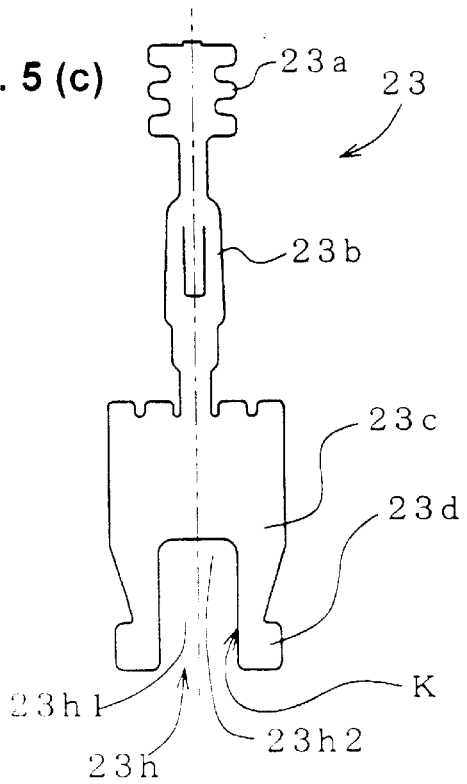

FIG. 5 shows the details of the metallic internal-electrode connection member 23. A blank shown in the development of FIG. 5(c) is blanked out from a conductive sheet and is formed into the metallic internal-electrode connection member 23, which includes the following integral portions: the connector 23a, the lead portion 23b, the engagement portion 23c, the press portion 23d, and the diameter reduction portion 23e. The engagement portion 23c is formed by bending so as to assume a substantially horseshoe-like cross section taken perpendicularly to the axis that has the opening 23c1 formed at a circumferential portion thereof. By bending, the press portion 23d is formed so as to assume a substantially L-shaped cross section; the connector 23a is formed so as to include an upright portion; and the flange 23g is formed so as to extend radially outward.

In the course of bending the engagement portion 23c located at the base-end side relative to the insertion direction into the hollow portion 2a of the oxygen detection element 2, the diameter reduction portion 23e-which is located adjacent to the engagement portion 23c and at the front-end side relative to the insertion direction-is formed concurrently. The diameter reduction portion 23e includes a first portion 23e1 and a second portion 23e2. The first portion 23e1 is axially tapered such that the size decreases toward the front-end side relative to the insertion direction into the hollow portion 2a of the oxygen detection element 2. In the front view (FIG. 5(b)); i.e., as observed in the longitudinal section which includes the opening 23c1 and the center axis of the metallic internal-electrode connection member 23, the width (radial dimension) in a direction perpendicular to the axis changes continuously. The first portion 23e1 serves as a guide for smooth insertion of the engagement portion 23c into the hollow portion 2a of the oxygen detection element 2. The second portion 23e2 is formed such that, as observed in the longitudinal section (FIG. 5(b)) which includes the opening 23c1 and the center axis of the metallic internal-electrode connection member 23, the radial dimension changes stepwise at its base-end side relative to the insertion direction.

A cut 23h of a substantially constant width is formed in the second portion 23e2 of the diameter reduction portion 23e in such a manner as to extend from an opening 23h1 located at the front-end side relative to the insertion direction toward a bottom 23h2 located at the base-end side relative to the insertion direction. On the development (FIG. 5(c)), a cut line K assumes the form of an inverted cup. In the front view (FIG. 5(b)), an outline G of the cut assumes substantially the form of an inverted letter L.

Figures 6A, 6B, 6C:
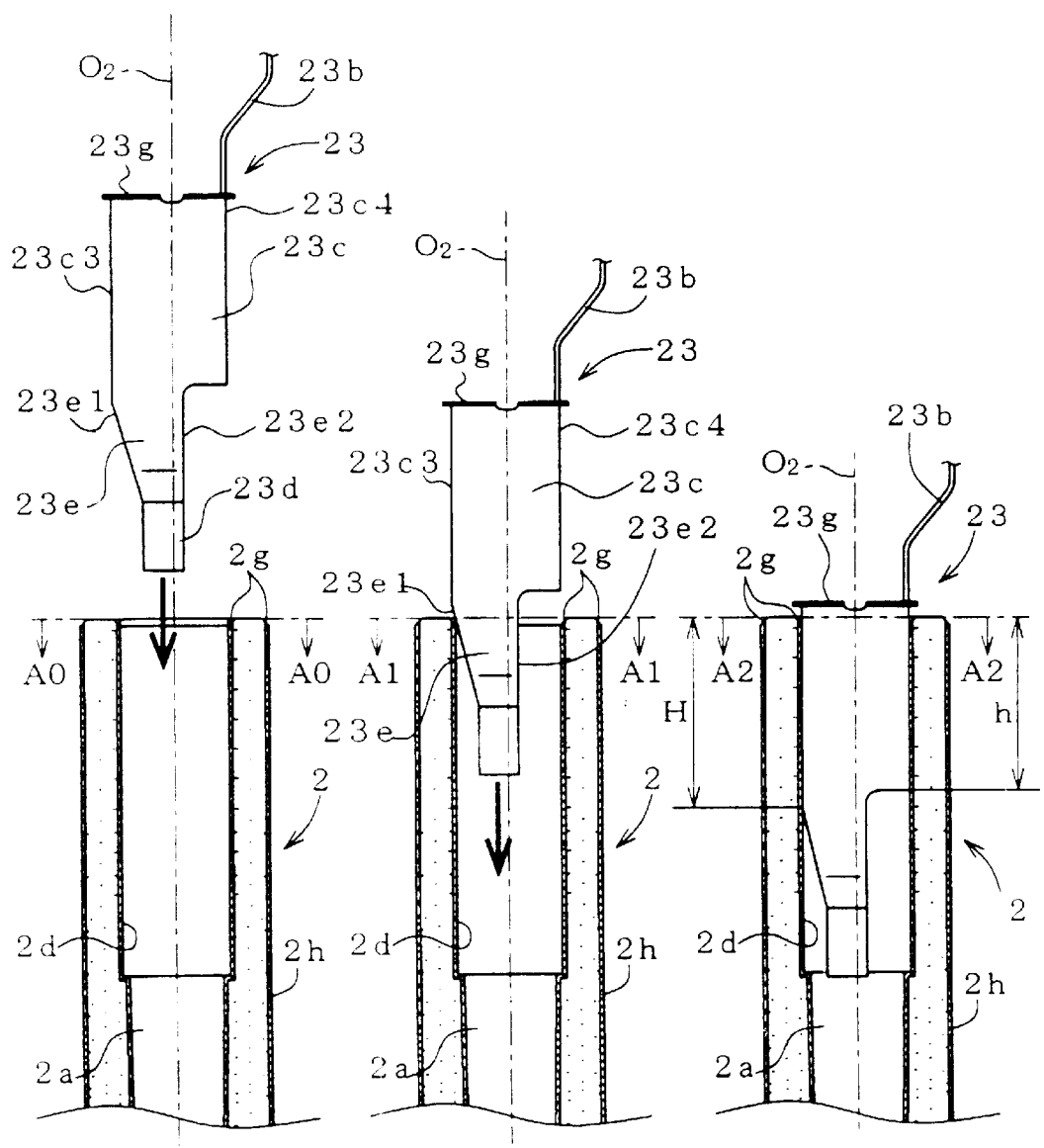
FIGS. 6(a), 6(b) and 6(c) show explanatory views showing an example of a procedure for installing the metallic internal-electrode connection member into the oxygen detection element.
Figure 7:
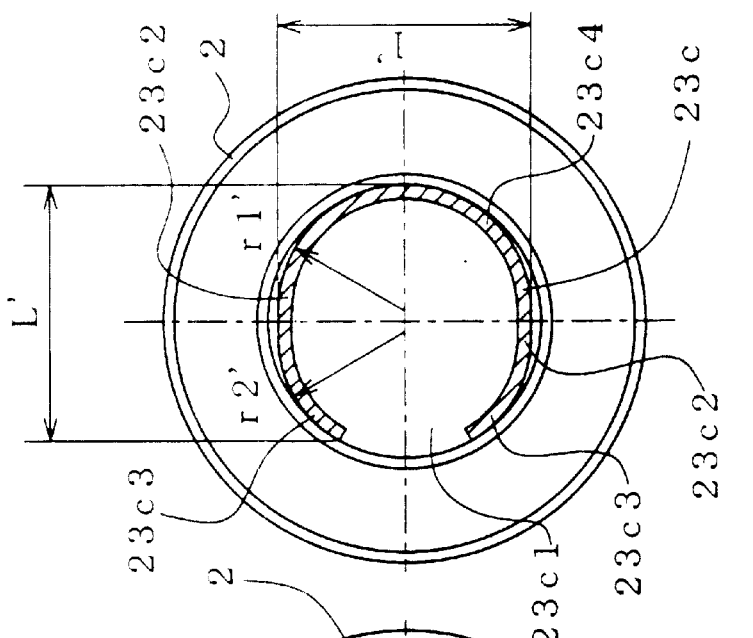
FIGS. 7(a), 7(b) and 7(c) show transverse sectional views of FIG. 6.
Figure 7:
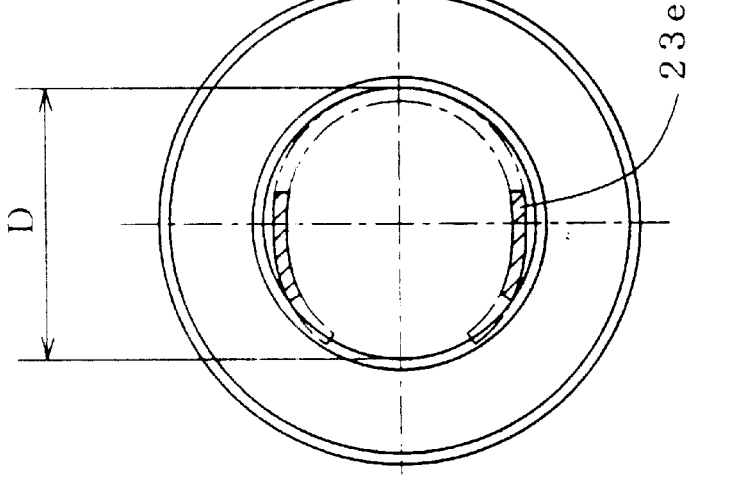
Figure 7:
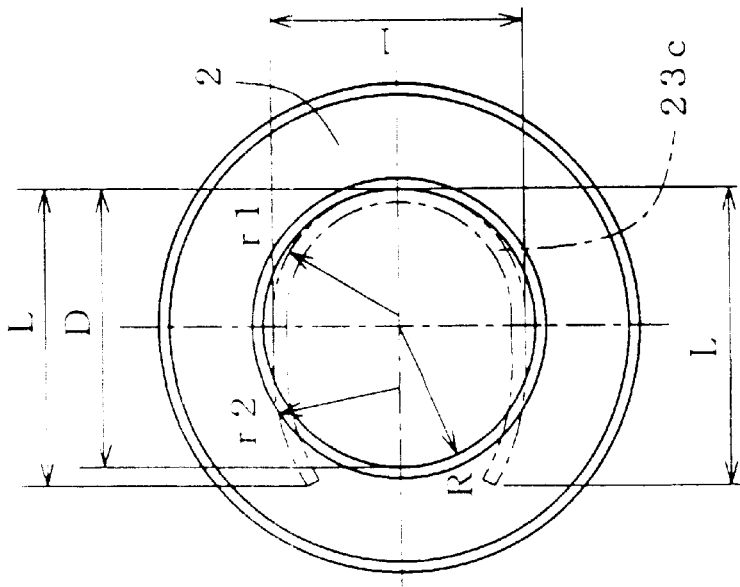
Figure 8:
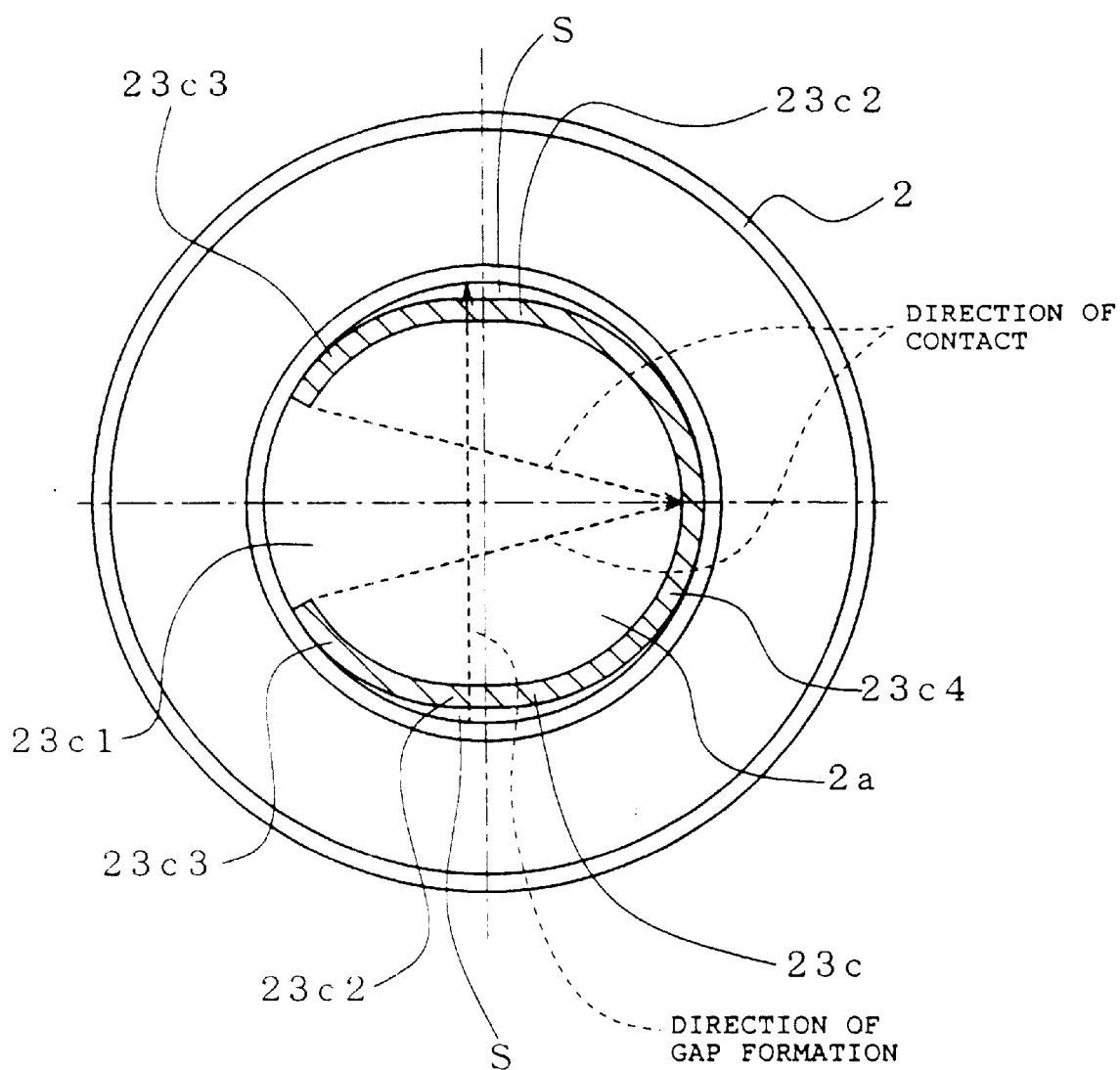
FIG. 8 is a cross-sectional view showing a state in which the metallic internal-electrode connection member is installed in the oxygen detection element.

FIG. 6 shows explanatory views depicting an example of installation of the metallic internal-electrode connection member into the oxygen detection element. FIG. 7 shows transverse sectional views of the hollow portion (counter-bore portion) of the oxygen detection element taken at the rear-end opening portion thereof and corresponding to the views of FIG. 6. FIG. 8 is a transverse sectional view showing installation of the metallic internal-electrode connection member 23 in the oxygen detection element. The metallic internal-electrode connection member 23 is positioned above the hollow portion 2a, having a substantially circular cross section, of the oxygen detection element 2 (FIGS. 6(a) and 7(a)). Then, the metallic internal-electrode connection member 23 is gradually lowered while a portion of the outer circumferential surface of the engagement portion 23c corresponding to the lead portion 23b is used as a reference for insertion. At and after the time when an intermediate portion of the first portion 23e1 of the engagement portion 23c comes into contact with the rear end of the hollow portion 2a (counter-bore portion 2d), the engagement portion 23c is squeezed inward from opposite contact sides (FIGS. 6(b) and 7(b)). While being subjected to resistance of insertion associated with squeezing of the engagement portion 23c, the metallic internal-electrode connection member 23 is further lowered down to a predetermined position (FIGS. 6(c) and 7(c)). By virtue of a resilient force associated with squeezing of the engagement portion 23c, a portion of the outer circumferential surface of the metallic internal-electrode connection member 23 is brought into reliable and secure contact with the inner wall surface of the hollow portion 2a of the oxygen detection element 2. Notably, FIG. 6 shows explanatory views depicting the positional relationship in installing the metallic internal-electrode connection member 23 in the oxygen detection element 2 and does not show an actual procedure for installing the metallic internal-electrode connection member 23 in the oxygen detection element 2.

The engagement portion 23c of the metallic internal-electrode connection member 23 is disposed such that, as observed in cross section, the engagement portion 23c is in contact with the inner wall surface of the hollow portion 2a of the oxygen detection element 2 at opposite sides thereof located along a predetermined direction (hereinafter called the direction of contact), and a gap is formed between the engagement portion 23c and the inner wall surface of the hollow portion 2a of the oxygen detection element 2 at opposite sides thereof located along a direction intersecting the direction of contact (hereinafter called the direction of gap formation). Specifically, as observed in cross section, the engagement portion 23c has an opening 23c1 formed at a portion of the circumference thereof and includes a direction change portion 23c4, which is located opposite the opening 23c1 with respect to the axis. The engagement portion 23c assumes the form of a horseshoe-like cross section, which is composed of an outwardly-projecting curve and a straight line. The engagement portion 23c is disposed within the hollow portion 2a such that edge portions 23c3 located at opposite sides of the opening 23c1 and the direction change portion 23c4 are in contact with the inner wall surface of the hollow portion 2a. According to the present embodiment, a direction extending between the direction change portion 23c4 and one of the edge portions 23c3 located at opposite sides of the opening 23c1 is the direction of contact (see FIG. 8). The engagement portion 23c, as observed in cross section, includes parallel portions 23c2 which are located opposite each other along a direction of gap formation, which intersects the direction of contact. Thus, the engagement portion 23c is disposed within the hollow portion 2a such that a gap S is formed at opposite sides thereof located along the direction of gap formation (see FIG. 8). As shown in FIG. 8, the direction of contact and the direction of gap formation intersect each other, but not necessarily in a perpendicularly intersecting relation. Thus, merely a portion of the outer circumferential surface of the engagement portion 23c is in contact with the inner wall surface of the hollow portion 2a, thereby suppressing to a low level the resistance of insertion of the metallic internal-electrode connection member 23 into the oxygen detection element 2.

As shown in FIG. 8, the engagement portion 23c includes the linear parallel portions 23c2, which are each circumferentially apart from the opening 23c1 by about 90° and which face each other. The edge portions 23c3 located at opposite sides of the opening 23c1 and the semicircular direction change portion 23c4, which is located opposite the opening 23c1 with respect to the axis, serve as contact portions. As a result, the engagement portion 23c is disposed so as to be in contact with the inner wall surface of the hollow portion 2a of the oxygen detection element 2 at the three portions-the edge portions 23c3 located at the opposite sides of the opening 23c1 and the direction change portion 23c4-and such that gaps are formed at opposite sides located along the direction of gap formation. Accordingly, in the state in which the engagement portion 23c is inserted into the hollow portion 2a of the oxygen detection element 2, as observed in cross section, L' (hereinafter called a radial dimension after insertion) is greater than 1' (1'<L' in FIG. 7(c)), where L' is the distance between opposite points of the engagement portion 23c located along the direction of contact and as projected on the line passing through the center of the width of the opening 23c1 and the center of the hollow portion 2a, and 1' is the dimension of the engagement portion 23c as measured in the direction of gap formation. Also, in the state before the engagement portion 23c is inserted into the hollow portion 2a of the oxygen detection element 2, as observed in cross section, L (hereinafter called a radial dimension before insertion) is greater than 1 (1<L in FIG. 7(a)), where L is the distance between opposite points of the engagement portion 23c located along the direction of contact and as projected on the line passing through the center of the width of the opening 23c1 and the center of the hollow portion 2a, and 1 is the dimension of the engagement portion 23c as measured in the direction of gap formation.

In the state before the metallic internal-electrode connection member 23 is inserted into the hollow portion 2a of the oxygen detection element 2, the radial dimension L before insertion of the engagement portion 23c is equal to or greater than inside diameter D of the oxygen detection element 2 (D≦L). By virtue of a resilient force associated with squeezing of the engagement portion 23c, the inserted engagement portion 23c is in reliable and secure contact with the inner wall surface of the hollow portion 2a of the oxygen detection element 2.

Before the metallic internal-electrode connection member 23 is inserted into the hollow portion 2a of the oxygen detection element 2, the engagement portion 23c is formed such that, in any cross section at an engagement 23f, the distance between the direction change portion 23c4 serving as a reference position and the edge portion 23c3 located at one side of the opening 23c1 is substantially equal to the distance between the direction change portion 23c4 and the edge portion 23c3 located at the other side of the opening 23c1 (see FIG. 7(a)). Also, before the metallic internal-electrode connection member 23 is inserted into the hollow portion 2a of the oxygen detection element 2, as observed in a longitudinal section which includes the opening 23c1 and the center axis of the metallic internal-electrode connection member 23, the edge portions 23c3 located at opposite sides of the opening 23c1 extend linearly in the direction of the axis of the hollow portion 2a of the oxygen detection element 2 (see FIG. 5(a)). As observed in a longitudinal section which includes the opening 23c1 and the center axis of the metallic internal-electrode connection member 23, the direction change portion 23c4 extends linearly in the direction of the axis of the hollow portion 2a of the oxygen detection element 2 (see FIG. 6(a)). Thus, further smooth insertion of the metallic internal-electrode connection member 23 becomes possible, and chipping of the internal electrode layer 2c is less likely to occur.

The diameter reduction portion 23e is formed at the front side of the engagement portion 23c. The diameter reduction portion 23e extends continuously from the edge portions 23c3 located at opposite sides of the opening 23c1 in the direction of insertion of the metallic internal-electrode connection member 23 into the hollow portion 2a of the oxygen detection element 2 and is tapered such that the size decreases toward the front-end side relative to the insertion direction. The metallic internal-electrode connection member 23 is inserted into the hollow portion 2a of the oxygen detection element 2 while the diameter reduction portion 23e is guided by the hollow portion 2a and such that insertion of the engagement portion 23c follows insertion of the diameter reduction portion 23e (see FIG. 6(b)). Since the metallic internal-electrode connection member 23 is inserted into the hollow portion 2a of the oxygen detection element 2 while the diameter reduction portion 23e is guided by the hollow portion 2a, the resistance of insertion in the course of assembly is reduced, and the inserted metallic internal-electrode connection member 23 is in reliable and secure contact with the inner wall surface of the hollow portion 2a. According to the present embodiment, the entire first portion 23e1 is tapered. However, a portion of the first portion 23e1 may be tapered. In FIG. 6, the first portion 23e1 is tapered linearly. However, the first portion 23e1 may be tapered in a curved manner. The range (length, inclination, etc.) over which a squeezing action is exerted on the engagement portion 23c in the direction of contact is not limited to that illustrated, but may be selected as appropriate.

The length H of contact of the edge portions 23c3 located at opposite sides of the opening 23c1 of the engagement portion 23c as measured axially from the end face of the rear-end opening portion of the oxygen detection element 2 is rendered longer than the length h of contact of the direction change portion 23c4 of the engagement portion 23c as measured axially from the end face of the rear-end opening portion of the oxygen detection element 2 (see FIG. 6(c)). Upon start of insertion of the engagement portion 23c into the oxygen detection element 2, the radial dimension of the engagement portion 23c is equal to that of the diameter reduction portion 23e, which is smaller than the inside diameter D of the oxygen detection element 2 (FIG. 7(b)). Accordingly, insertion of the engagement portion 23c into the hollow portion 2a of the oxygen detection element 2 becomes very smooth. The first portion 23e1 to be squeezed in the course of insertion first comes into contact with the rear-end opening portion of the oxygen detection element 2. Then, as insertion of the engagement portion 23c progresses, the engagement portion 23c is elastically deformed in such a manner as to be squeezed radially inward, so that the resistance of insertion is suppressed to a low level.

In the state in which the engagement portion 23c is inserted into the oxygen detection element 2, at a contact portion between the engagement portion 23c of the metallic internal-electrode connection member 23 and the inner wall surface of the hollow portion 2a of the oxygen detection element 2, a radius of curvature r' of the outer circumferential surface of the engagement portion 23c is smaller than a radius of curvature R of the inner wall surface of the hollow portion 2a. Specifically, regarding the contact portions located in the direction of contact in FIG. 7(c), a radius of curvature r2' of the outer circumferential surface of the edge portion 23c3 located at either side of the opening 23c1 is smaller than the radius of curvature R of the inner wall surface of the hollow portion 2a; and a radius of curvature r1' of the outer circumferential surface of the direction change portion 23c4 is smaller than the radius of curvature R (r1'<R; r2'<R). Thus, the area of contact decreases at the contact portions, thereby reducing the resistance of insertion in the course of assembly. Similarly, in the case of the engagement portion 23c before insertion into the oxygen detection element 2, a radius of curvature r2 of the outer circumferential surface which is of the edge portion 23c3 located at either side of the opening 23c1 and which is to abut the inner wall surface of the hollow portion 2a is smaller than the radius of curvature R of the inner wall surface of the hollow portion 2a; and a radius of curvature r1 of the outer circumferential surface which is of the direction change portion 23c4 located opposite the edge portion 23c3 with respect to the axis of the hollow portion 2a and which is to abut the inner wall surface of the hollow portion 2a is smaller than the radius of curvature R of the inner wall surface of the hollow portion 2a (r1<R; r2<R (FIG. 7(a)).

The counter-bore portion 2d is formed in a rear-end opening portion of the hollow portion 2a of the oxygen detection element 2 in a diameter expanded-manner so as to receive the engagement portion 23c. Thus, the engagement 23c becomes less susceptible to deformation or breakage which could occur due to forcible insertion into the hollow portion 2a of the oxygen detection element 2, and becomes less susceptible to play or coming-off which would could occur due to exposure to repeated vibration.

FIG. 9 shows the state in which the engagement portion 23 of the metallic internal-electrode connection member 23 is removed from the hollow portion 2a while being elastically restored from the state of FIGS. 6(c) and 7(c) in which the engagement portion 23c is inserted into the hollow portion 2a of the oxygen detection element 2 while being elastically deformed radially inward. In the removed state of FIG. 9 and as observed in cross section, La (hereinafter called a radial dimension after removal) is equal to or greater than D (D≦La in FIG. 9(b)) and greater than 1a (1a<La in FIG. 9(b)), where La is the distance between opposite points of the engagement portion 23c located along the direction of contact and as projected on the line passing through the center of the width of the opening 23c1 and the center of the hollow portion 2a; D is the inside diameter of the oxygen detection element 2; and 1a is the dimension of the removed engagement portion 23c as measured in the direction of gap formation. Notably, in the case of the engagement portion 23c after removal from the oxygen detection element 2, a radius of curvature r2a of the outer circumferential surface which is of the edge portion 23c3 located at either side of the opening 23c1 and which is released from abutment is smaller than the radius of curvature R of the inner wall surface of the hollow portion 2a; and a radius of curvature r1a of the outer circumferential surface which is of the direction change portion 23c4 located opposite the edge portion 23c3 with respect to the axis of the hollow portion 2a and which is released from abutment is smaller than the radius of curvature R of the inner wall surface of the hollow portion 2a (r1a<R; r2a<R (FIG. 9(b)).

In the course of insertion ranging from the step of FIG. 6(a) to the step of FIG. 6(c), the engagement portion 23c is inserted into the hollow portion 2a of the oxygen detection element 2 in such a manner as to be elastically deformed in a radially inward direction. In the course of removal ranging from the step of FIG. 6(c) to the step of FIG. 9(a), the engagement portion 23c is removed from the hollow portion 2a of the oxygen detection element 2 in such a manner as to be elastically restored in a radially outward direction. If the above-mentioned insertion and removal involve only elastic deformation without involvement of plastic deformation, dimensions of segments of the engagement portion 23c will be restored to those as measured before insertion. Specifically, La=L; 1a=1; r1a=r1; and r2a=r2. Even when slight plastic deformation is involved, these dimensional relations may be considered to hold approximately true.

Figure 10:
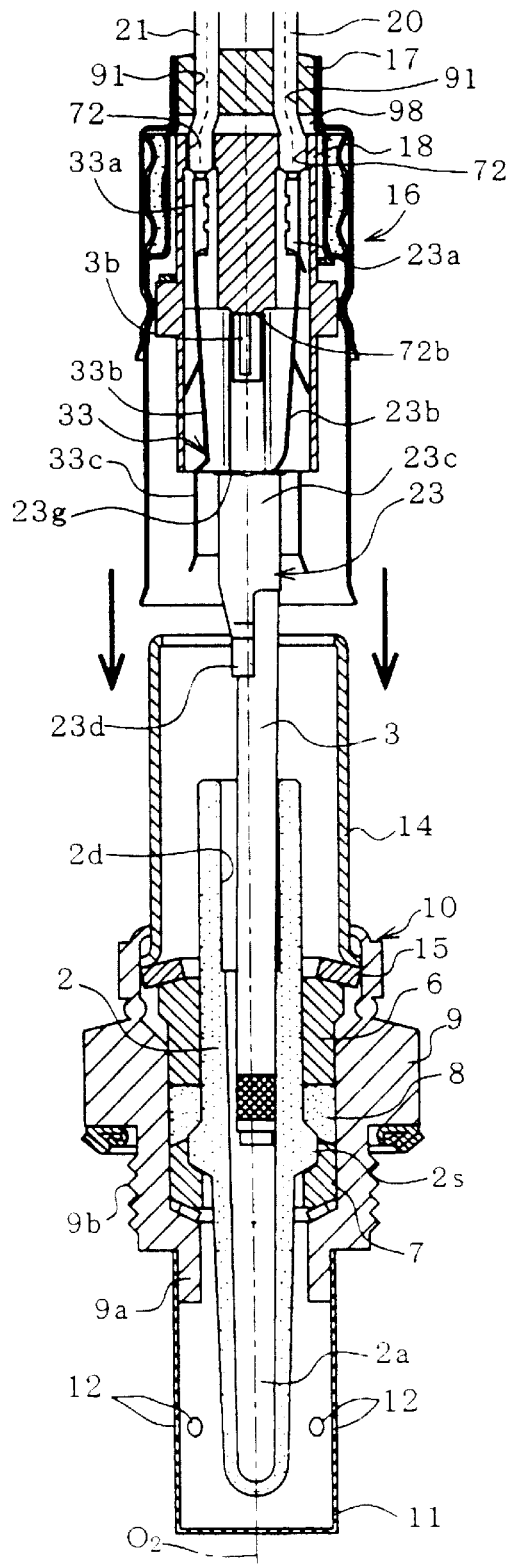
FIGS. 10(a) and 10(b) show views showing an example of an assembling procedure for the oxygen sensor of FIG. 1.

FIG. 10 shows an example of an assembling procedure for an oxygen sensor. First, the heating member 3 is inserted into the metallic internal-electrode connection member 23 from the rear side. The heating member 3 is held in radial directions by the press portion 23d of the metallic internal-electrode connection member 23. In this state, the lead wire 20 connected to the metallic internal-electrode connection member 23 is led to the outside through the lead wire through-hole 72 formed in the ceramic separator 18 and then through the lead wire through-hole 91 formed in the grommet 17. The metallic internal-electrode connection member 23 is disposed such that the flange 23g abuts the front-end face of the ceramic separator 18. The rear-end portion of the heating member 3 rests on the bottom surface 72b of the heating-member-end-portion accommodation hole 72a, whereby the heating member 3 is axially positioned. The lead wire 21 connected to the metallic external-electrode connection member 33 is sequentially led to the outside through the lead wire through-holes 72 and 91. In a separate step, the oxygen detection element 2 is installed in the casing 10. The rear-end side of the casing 10, in which the oxygen detection element 2 is installed, and the front-end side of the filter assembly 16, in which the metallic electrode connection members 23 and 33 and the heating member 3 are installed, are caused to relatively approach each other. As a result, the heating member 3 is gradually inserted into the hollow portion 2a of the oxygen detection element 2, while the inner wall surface of the hollow portion 2a serves as a guide (FIG. 10(a)). Herein, the expression "relatively approach" denotes that either the casing 10 or the filter assembly 16 is moved while the other is held stationary or that both the casing filter 10 and the filter assembly 16 are moved in opposite directions, thereby causing both to approach each other.

Then, the engagement portion 23c of the metallic internal-electrode connection member 23 is inserted into the hollow portion 2a of the oxygen detection element 2 through the rear-end opening portion of the hollow portion 2a such that the external surface of the engagement portion 23c is fitted to the wall surface of the counter-bore 2d. At substantially the same time, the outer circumferential surface of the oxygen detection element 2 is inserted into the metallic exterior-electrode connection member 33. At this time, the press portion 23d press the heating member 3 in a direction intersecting the center axis $O_2$ of the hollow portion 2a of the oxygen detection element 2, whereby the heating member 3 is brought into contact with the inner wall surface of the hollow portion 2a of the oxygen detection element 2 in the entire contact state. When a predetermined insertion position is reached, the grommet 17 and the first filter holder 51 are caulked together to thereby form a grommet-caulked portion 67. The frictional force F generated on the contact surfaces of the grommet 17 and the lead wire 20 serves as holding means for holding the heating member 3. Finally, a casing-caulked portion 76 is formed (FIG. 10(b)).

The above-mentioned procedure for assembling the oxygen sensor 1 is less likely to involve deformation of portions of the metallic internal-electrode connection member 23 in the course of insertion of the metallic internal-electrode connection member 23 into the hollow portion 2a of the oxygen detection element 2, and disposes the metallic internal-electrode connection member 23 such that the center axis of the metallic internal-electrode connection member 23 is substantially in parallel with the center axis $O_2$ of the hollow portion 2a of the oxygen detection element 2. When the heating member 3 is inserted into the metallic internal-electrode connection member 23, the heating member 3 is reliably and fixedly positioned such that the surface of the heating member 3 is in the state of overall contact (or in the state of near overall-contact) with the inner wall surface of the hollow portion 2a of the oxygen detection element 2.

Figure 12:
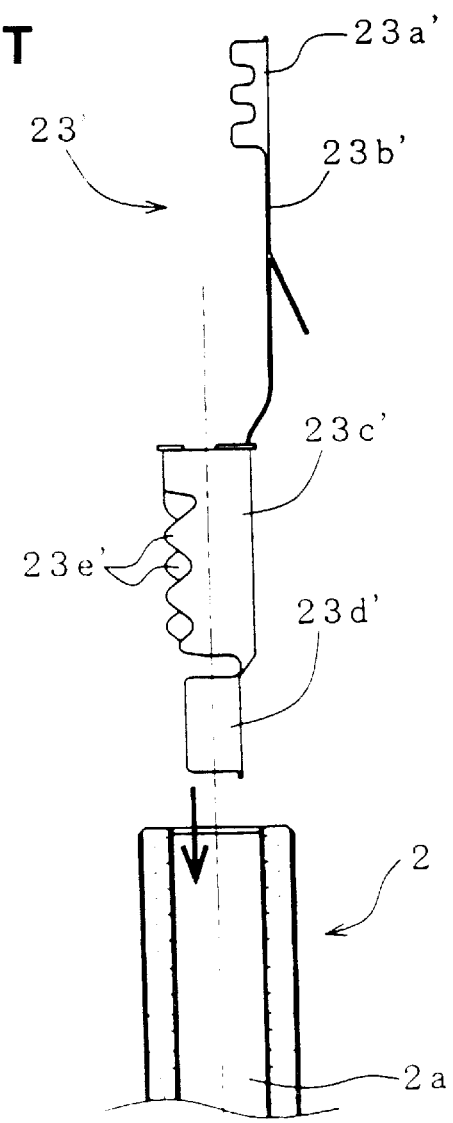
FIG. 12 is a reference view showing installation of a conventional metallic internal-electrode connection member into a conventional oxygen detection element.

Specifically, in the conventional type shown in FIG. 12 in which a plurality of saw-toothed portions are arranged at opposite sides in a staggered manner, the resistance of insertion tends to occur intermittently at the contact portions 23e'. Also, due to plastic deformation of the metallic internal-electrode connection member 23', the center axis of the metallic internal-electrode connection member 23' may deviate from that of the hollow portion 2a of the oxygen detection element 2. This axis deviation potentially causes instability in lateral abutment. However, in the present embodiment, the edge portions 23c3 located at opposite sides of the opening 23c1 of the engagement portion 23c extend linearly in the direction of the axis of the hollow portion of the oxygen detection element, thereby reducing the resistance of insertion. As a result, a potential deviation of the center axis of the metallic internal-electrode connection member 23 from the center axis $O_2$ of the hollow portion 2a of the oxygen detection element 2 is suppressed, thereby stably maintaining the lateral abutment state of the heating member 3.

In the course of inserting the metallic internal-electrode connection member into the hollow portion of the oxygen detection element, the occurrence of a large resistance of insertion or the intermittent occurrences of the resistance of insertion as in the case of the contact portions 23e' of FIG. 12 may cause chipping on the front-end face of the ceramic separator, which abuts the rear end of the engagement portion of the metallic internal-electrode connection member. The present embodiment can sufficiently suppress this chipping of the ceramic separator by virtue of devices for reducing the resistance of insertion. The contact area of the flange 23g, which abuts the ceramic separator, may be sufficiently increased so as to disperse the resistance of insertion, thereby preventing the occurrence of chipping.

Figure 11:
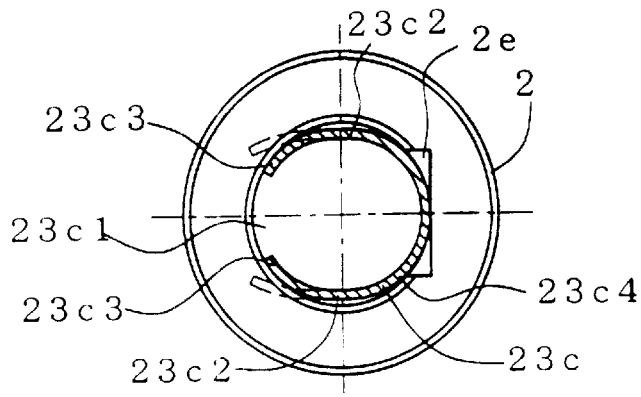
FIG. 11 is a transverse sectional view showing another embodiment of the form of the oxygen detection element of FIG. 7.

FIG. 11 is a transverse sectional view showing another embodiment of the form of the oxygen detection element shown in FIG. 7. In FIG. 7(a), the direction change portion 23c4 serving as a contact portion is located opposite the edge portion 23c3 with respect to the axis, and the radius of curvature r1 of the outer circumferential surface of the direction change portion 23c4 which is to abut the inner wall surface of the hollow portion 2a is smaller than the radius of curvature R of the inner wall surface of the hollow portion 2a (r1<R), thereby reducing the area of contact so as to reduce the resistance of insertion in the course of assembly. However, the difference between the radiuses of curvature is small. Accordingly, as the engagement portion 23c is inserted into the hollow portion 2a, the area of contact (the resistance of insertion) of the direction change portion 23c4, which serves as an arcuate contact portion, increases. Thus, in FIG. 11, a groove 2e which opens toward the center of the hollow portion 2a is formed on a portion of the inner wall surface of the hollow portion 2a of the oxygen detection element 2 (or the inner wall surface of the counter-bore portion 2d) and extends axially over at least the length h of contact with the engagement portion 23c. The direction change portion 23c4 serving as an arcuate contact portion abuts the bottom of the groove 2e, thereby suppressing an increase in the area of contact (the resistance of insertion) of the direction change portion 23c4, which serves as a contact portion in the course of insertion of the engagement portion 23c into the hollow portion 2a. Notably, the groove 2e can be formed in the course of compacting of the oxygen detection element 2.

Figure 13:
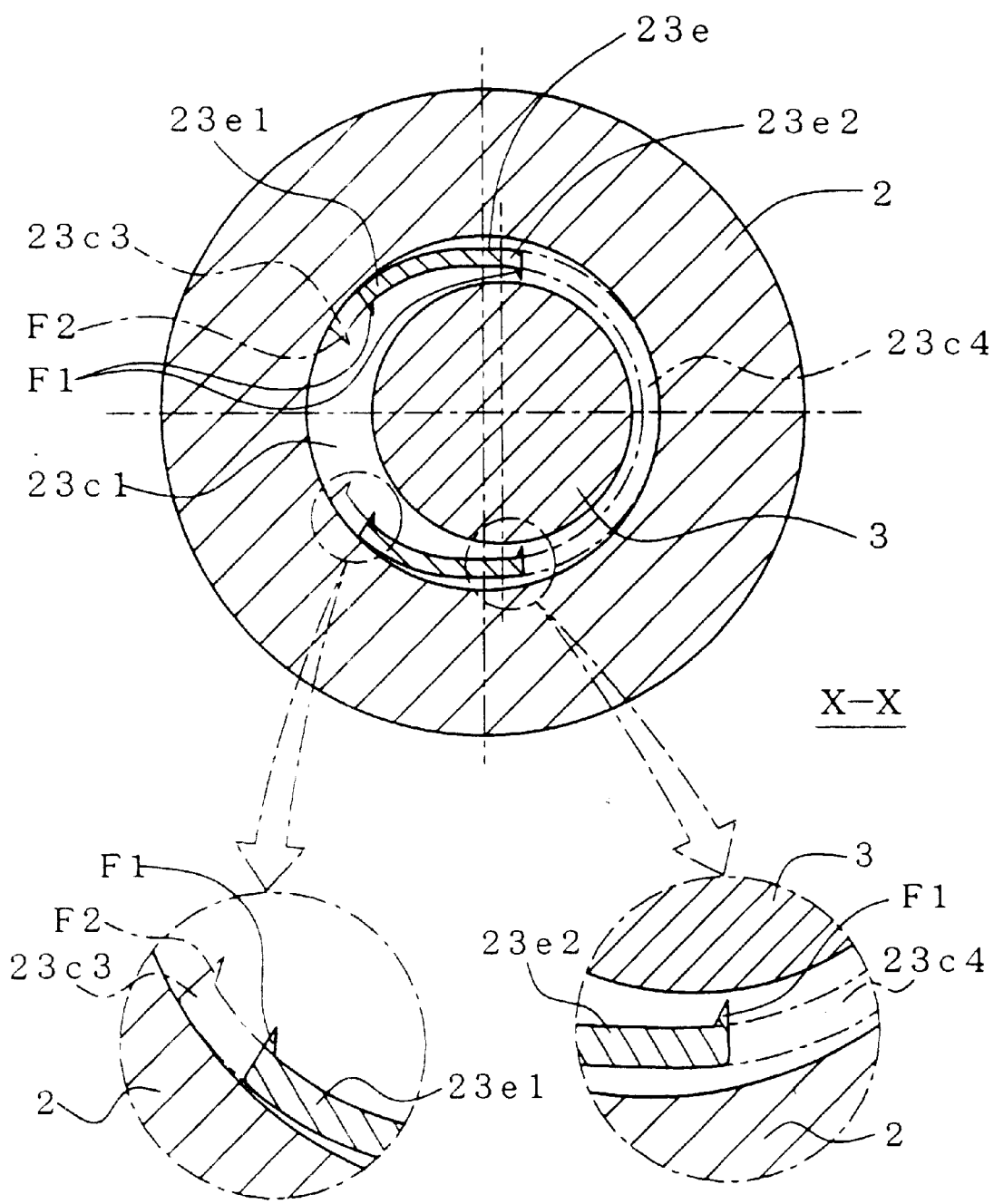
FIG. 13 is a sectional view taken along X—X of FIG. 4.

FIG. 13 is a sectional view taken along X—X of FIG. 4, showing the cross section of the diameter reduction portion 23e of the metallic internal-electrode connection member 23 in a state in which the metallic internal-electrode connection member 23 and the heating member 3 are inserted into the hollow portion 2a of the oxygen detection element 2. As mentioned previously, the blank shown in the development of FIG. 5(c) is blanked out from a conductive sheet and is formed into the metallic internal-electrode connection member 23 through bending. Bending is performed such that burrs which have been formed in the course of blanking are located at the inside of bending; i.e., such that burrs F1 are located on the inner-surface side of the engagement portion 23c which is formed into a cylindrical form through bending. Accordingly, in a state in which the metallic internal-electrode connection member 23 and the heating member 3 are inserted into the hollow portion 2a of the oxygen detection element 2, the burrs F1 on the diameter reduction portion 23e are located on the inner-surface side of the first and second portions 23e1 and 23e2; i.e., the burrs F1 project toward the heating member 3. Since the burrs F1 on the diameter reduction portion 23e do not project on the outer-surface side, in the course of insertion of the diameter reduction portion 23e into the hollow portion 2a of the oxygen detection element 2, the internal electrode layer 2c formed on the inner wall surface of the hollow portion 2a does not suffer scraping, which might impair electrical conductivity. Also, at the edge portions 23c3 located at opposite sides of the opening 23c1, burrs F2 on the engagement portion 23c do not project on the outer-surface side. Thus, as in the above-mentioned case, the internal electrode layer 2c is not susceptible to impairment in electrical conductivity.

Figure 14:
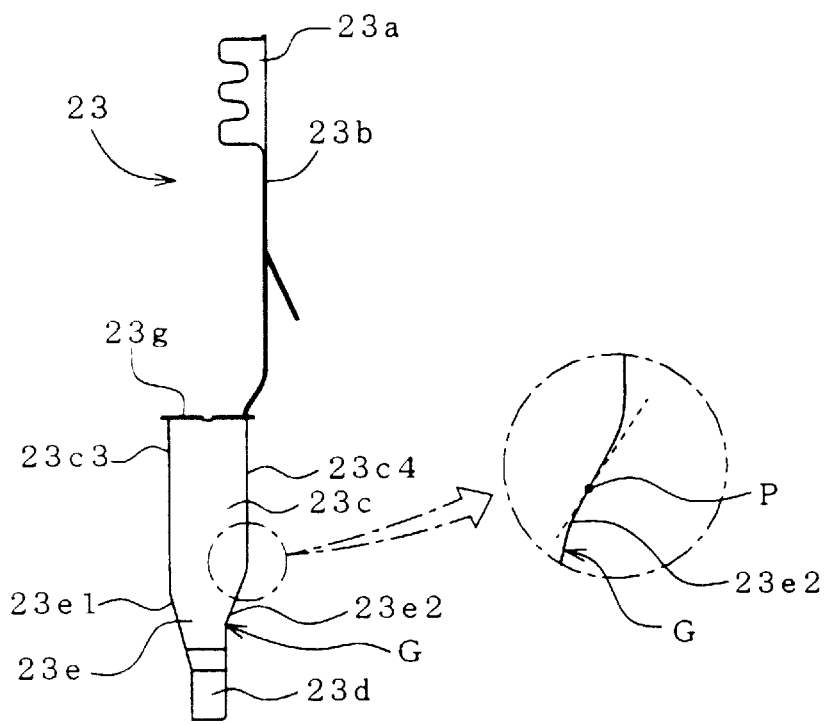
FIG. 14(a) is a front view showing a first modified embodiment of the metallic internal-electrode connection member of FIG. 5, and FIGS. 14(b), 14(c) and 14(d) are developments showing three corresponding kinds of modifications.
Figure 14:
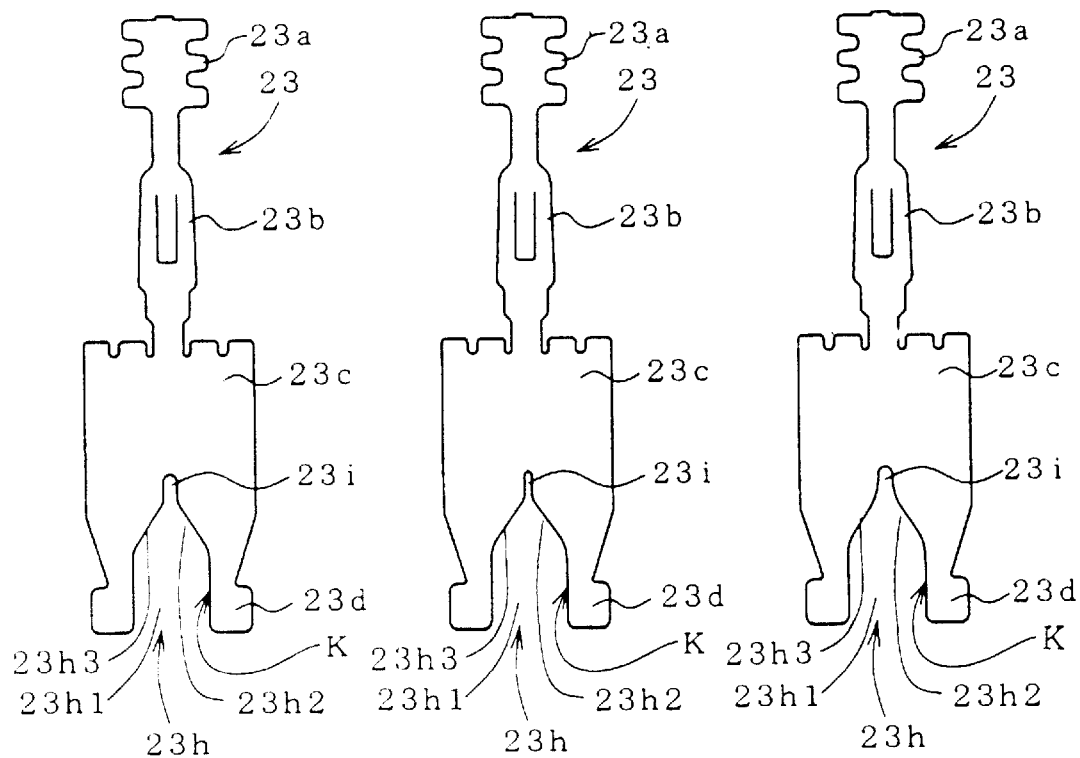
Figure 15:
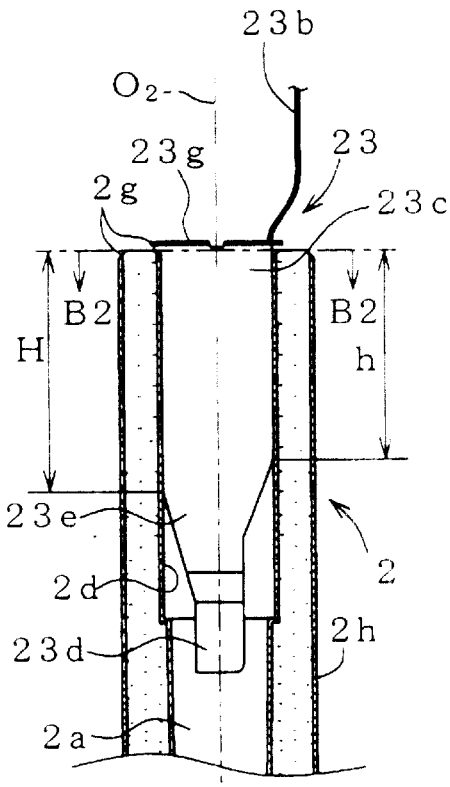
FIGS. 15(a), 15(b) and 15(c) show explanatory views and a transverse sectional view showing an example of a procedure for installing the metallic internal-electrode connection member into the oxygen detection element.
Figure 15:
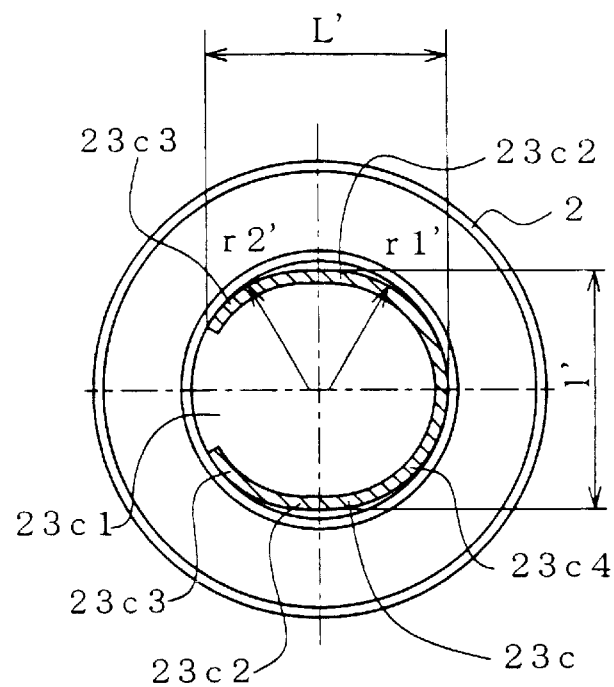
Figure 15:
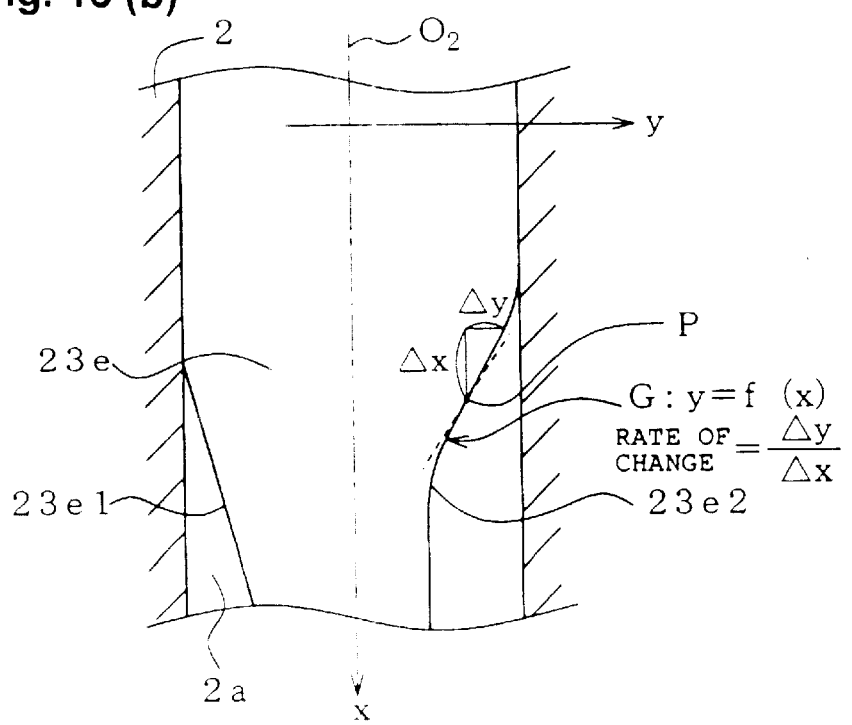

FIG. 14(a) is a front view showing a first modified embodiment of the metallic internal-electrode connection member of FIG. 5. FIGS. 14(b) to 14(d) are developments showing three examples of the metallic internal-electrode connection member of FIG. 14(a). FIG. 15 shows an example of installation of the FIG. 14 into the oxygen detection element. The present modified embodiment involves the following cut-related modifications (A)–(E). Features common to the embodiment of FIG. 5 are denoted by common reference numerals, and repeated description thereof is omitted.

(A) A reduction portion 23h3 is formed at a bottom 23h2 of a cut 23h such that the width along the circumferential direction of the inner wall surface of the hollow portion 2a of the oxygen detection element 2 decreases continuously toward the base-end side relative to the insertion direction. Specifically, the reduction portion 23h3 assumes the form of an inverted letter V. The reduction portion 23h3 formed at the bottom 23h2 of the cut 23h contributes to a great reduction in the resistance of insertion of the diameter reduction portion 23e in the course of insertion.

(B) An outline G of the cut 23h as projected on a longitudinal section which includes the bottom point of the cut 23h and the center axis $O_2$ of the metallic internal-electrode connection member 23 assumes such a form as to approach the inner wall surface of the hollow portion 2a toward the base-end side relative to the insertion direction. The second portion 23e2 is rounded at the base-end side thereof relative to the insertion direction, and the rounded portion comes into contact with the inner wall surface of the hollow portion 2a, thereby further reducing the resistance of insertion of the diameter reduction portion 23e in the course of assembly. Also, chipping of the internal electrode layer 2c becomes less likely to occur.

(C) The outline G includes a region in which the rate of change gradually decreases toward the inner wall surface of the hollow portion 2a, where the rate of change is represented by a fraction having a denominator indicative of the amount of change in the direction of insertion and a numerator indicative of the amount of change in a radially outward direction perpendicular to the direction of insertion. By forming the rate-of-change gradual-decrease region, at the base-end side of the second portion 23e2 relative to the insertion direction, the amount of approach in a radially outward direction (the amount of approach to the inner wall surface of the hollow portion 2a of the oxygen detection element 2) decreases gradually as the amount of insertion of the diameter reduction portion 23e increases. Thus, in the course of assembly, the resistance of insertion of the diameter reduction portion 23e further decreases.

In FIG. 15(b), the rate of change is represented in the following manner. The outline G of the cut 23h as projected on a longitudinal section which includes the bottom point of the cut 23h and the center axis $O_2$ of the metallic internal-electrode connection member 23 is represented by the function y=f(x), where the x axis represents the direction of insertion (the direction of the center axis $O_2$ of the hollow portion 2a), and the y axis represents a radial direction. The rate of change is represented by $\Delta y/\Delta x$, where $\Delta x$ is the amount of change in the direction of insertion, and $\Delta y$ is the amount of change in a radially outward direction.

(D) The outline G of the cut 23h includes an inflection point P at which the form of a radially inward convex shape at the front-end side thereof relative to the insertion direction changes to the form of a radially outward convex shape at the base-end side thereof relative to the insertion direction.

As shown in FIG. 14(a) or 15(b), the outline G is formed such that a portion located below the inflection point P assumes the form of a radially inward convex shape, whereas a portion located above the inflection point P assumes the form of a radially outward convex shape. The outline G of the cut 23h which includes the inflection point P yields the following advantage. While the second portion maintains a smooth outline, the rate of dimensional change in the axial direction (the direction of insertion) can be rendered great as compared to the rate of dimensional change in a radial direction. Thus, the radial size of the metallic terminal member can be reduced, whereby the oxygen detection element and the oxygen sensor can be formed to a compact size.

(E) The second portion 23e2 includes a sub-cut 23i formed therein extending from the bottom 23h2 of the cut 23h toward the base-end side relative to the insertion direction. Examples of the form of the sub-cut 23i include a groove form which has a predetermined width in the circumferential direction (see FIG. 14(b)); a slit form (linear form) which has almost no width in the circumferential direction (see FIG. 14(c)); and a tapered form (triangular form) having a circumferential width which continuously decreases toward the base-end side relative to the insertion direction (FIG. 14(d)). Formation of the sub-cut in the second portion of the diameter reduction portion causes the outline of the cut to include an inflection point. The inflection point enables the outline of the cut to include a rate-of-change gradual-decrease region.

Figure 16:
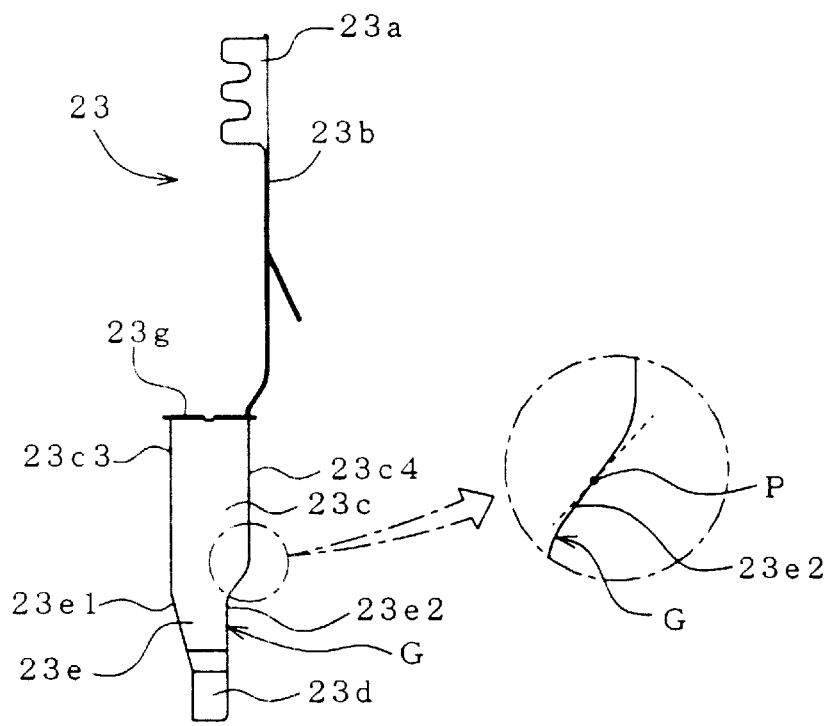
FIG. 16(a) is a front view showing a second modified embodiment of the metallic internal-electrode connection member of FIG. 5, and FIGS. 16(b), 16(c) and 16(d) are developments showing three corresponding kinds of modifications.
Figure 16:
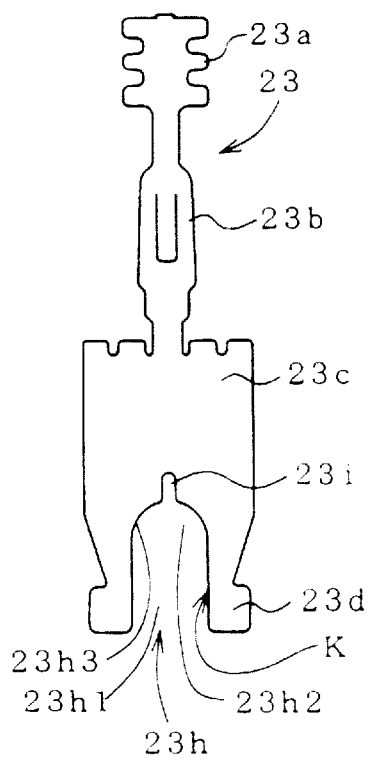
Figure 16:
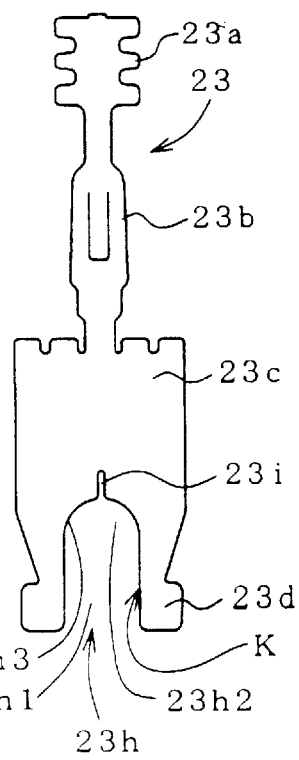
Figure 16:
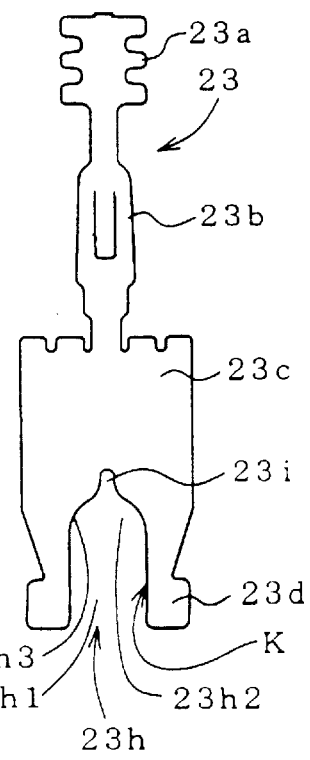

FIG. 16(a) is a front view showing a second modified embodiment of the metallic internal-electrode connection member of FIG. 5. FIGS. 16(b) to 16(d) are developments showing three examples of the metallic internal-electrode connection member of FIG. 16(a). As in the case of the first modified embodiment, the second modified embodiment involves the above-mentioned cut-related modifications (B)–(E). Cut-related modification (A) is partially modified as mentioned below in (A)'. Features common to the embodiment of FIG. 5 are denoted by common reference numerals, and repeated description thereof is omitted.

(A)' The reduction portion 23h3 is formed into a semicircle such that the width along the circumferential direction decreases continuously toward the base-end side relative to the insertion direction.

TEST EXAMPLES

In order to check the effect of the present invention in reducing the resistance of insertion in the course of insertion of the metallic internal-electrode connection member 23 (metallic terminal member) into the hollow portion 2a of the oxygen detection element 2, a test was conducted for measurement of the resistance of insertion. First, blanks which assumes a predetermined form and have been blanked out from a conductive sheet were formed through bending into 5 kinds of metallic internal-electrode connection members for test use. The forms of the metallic internal-electrode connection members for test use are shown in FIG. 17.

Figure 18:
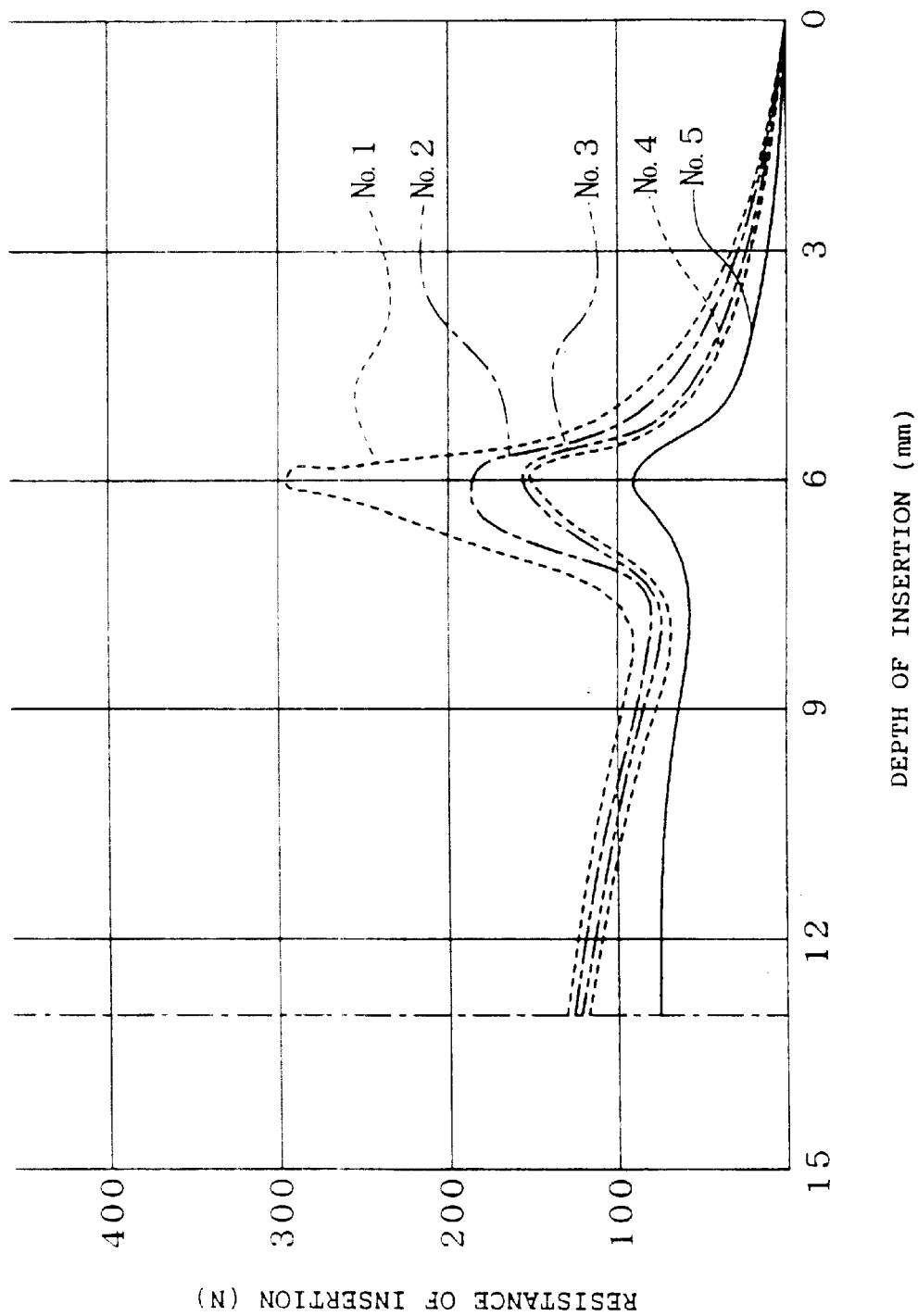
FIG. 18 is a graph showing test results of the relationship between the depth of insertion and the resistance of insertion.

As shown in FIG. 6, each of the oxygen detection elements 2 was installed in an assembly apparatus (not shown) for assembling the oxygen sensor 1, and each of the metallic internal-electrode connection members 23 for test use was inserted into the hollow portion 2a of the oxygen detection element 2. Subsequently, a curve indicative of the relationship between the resistance of insertion (load) and the depth of insertion (displacement) was automatically measured by means of an autographic recording device. The press force was 500 kgf, and the test speed was 50 mm/min. FIG. 18 shows the results of measurement.

The following is seen from FIG. 18.

(1) As a result of the metallic internal-electrode connection member 23 having a form such that, as observed on a cross section, gaps are formed at opposite sides in the direction of gap formation and such that a cut is formed in the second portion from the front end relative to the insertion direction toward the base-end side relative to the insertion direction, the resistance of insertion is substantially halved without involvement of intermittent occurrences of a peak of the resistance of insertion.

(2) As a result of the cut 23h having the reduction portion 23h3 formed such that the width along the circumferential direction decreases continuously toward the base-end side relative to the insertion direction, the resistance of insertion is reduced considerably (by about 100–150N at peak) effectively (No. 1 and No. 2), as compared with the case where the width along the circumferential direction reduces stepwise.

(3) Regarding the form of the reduction portion 23h3, which is formed on the cut 23h and such that the width along the circumferential direction decreases continuously toward the base-end side relative to the insertion direction, no particular difference is observed between the form of an inverted letter V and a semicircular form (No. 3 and No. 4). However, the form of an inverted letter V (No. 4)-in which the area of the diameter reduction portion 23e is relatively wide (the area of the cut is relatively narrow)-is preferred in terms of mechanical strength and attachment onto the inner wall surface of the hollow portion 2a of the oxygen detection element 2.

(4) The effect in reducing the resistance of insertion varies depending on the form of the sub-cut 23i. The sub-cut 23i having a slit form hardly yields effect in reducing the resistance of insertion. The sub-cut 23i having a groove form yields a considerable (by about 50–80N at peak) effect in reducing the resistance of insertion (No. 2 and No. 3; No. 4 and No. 5).

While the invention has been described in detail and with reference to specific examples thereof, it will be apparent to one skilled in the art that various changes and modifications can be made therein without departing from the spirit and scope thereof.

This application is based on Japanese Patent Application Nos. Hei. 11-177469 filed Jun. 23, 1999 and 2000–54935, filed Feb. 29, 2000, the disclosures of which are incorporated herein by reference in their entirety.

What is claimed is:

1. An oxygen sensor, comprising an oxygen detection element assuming a form of a hollow rod which is closed at one end, and having an electrode layer formed on at least an inner surface thereof, and a metallic terminal member electrically connected to the electrode layer, the oxygen sensor being characterized in that:

the metallic terminal member includes an attachment portion having a substantially circular cross section, which is disposed within a hollow portion of the oxygen detection element; and the attachment portion is disposed such that, as observed in cross section, the attachment portion is in contact with an inner wall surface of the hollow portion of the oxygen detection element at opposite sides thereof located along a predetermined direction of contact, and a gap is formed between the attachment portion and the inner wall surface of the hollow portion of the oxygen detection element at opposite sides thereof located along a direction of gap formation, intersecting the direction of contact.

2. The oxygen sensor as claimed in claim 1, wherein the attachment portion, as observed in cross section, has an opening formed at a portion of a circumference thereof and includes a direction change portion, which is located opposite the opening with respect to a center axis of the hollow portion of the oxygen detection element; and wherein edge portions located at opposite sides of the opening and the direction change portion are in contact with the inner wall surface of the hollow portion of the oxygen detection element, directly or indirectly via another member, and a direction extending between the direction change portion and one of the edge portions located at opposite sides of the opening is the direction of contact.

3. The oxygen sensor as claimed in claim 2, wherein, as observed in a longitudinal section which includes the opening and a center axis of the metallic terminal member, the edge portions located at opposite sides of the opening extend linearly in a direction of the axis of the hollow portion of the oxygen detection element.

4. The oxygen sensor as claimed in claim 2, wherein a diameter reduction portion is formed on the attachment portion at a front side relative to the insertion direction of the attachment portion into the hollow portion of the oxygen detection element; and, as observed in the longitudinal section which includes the opening and the center axis of the metallic terminal member, the diameter reduction portion includes a first portion, which is located adjacent to the edge portions located at opposite sides of the opening and which decreases in diameter continuously or stepwise at the front-end side relative to the insertion direction.

5. The oxygen sensor as claimed in claim 4, wherein the diameter reduction portion includes a second portion, which is located opposite the first portion with respect to the center axis of the hollow portion of the oxygen detection element and which, as observed in the longitudinal section which includes the opening and the center axis of the metallic terminal member, decreases in size continuously or stepwise toward the front-end side relative to the insertion direction.

6. The oxygen sensor as claimed in claim 5, wherein the second portion of the diameter reduction portion has a cut formed therein extending from a front end thereof relative to the insertion direction toward a base-end side relative to the insertion direction.

7. The oxygen sensor as claimed in claim 6, wherein a reduction portion is formed at a bottom of the cut such that a width along a circumferential direction of the inner wall surface of the hollow portion of the oxygen detection element decreases continuously toward the base-end side relative to the insertion direction.

8. The oxygen sensor as claimed in claim 6, wherein an outline of the cut as projected on a longitudinal section which includes a bottom point of the cut and the center axis of the metallic terminal member assumes such a form as to approach the inner wall surface of the hollow portion toward the base-end side relative to the insertion direction.

9. The oxygen sensor as claimed in claim 8, wherein the outline includes a region in which a rate of change gradually decreases toward the inner wall surface of the hollow portion, where the rate of change is represented by a fraction having a denominator indicative of an amount of change in a direction of insertion and a numerator indicative of the amount of change in a radially outward direction perpendicular to the direction of insertion.

10. The oxygen sensor as claimed in claim 8, wherein the outline includes an inflection point at which a radially inwardly convex form at the front-end side thereof relative to the insertion direction changes to a radially outwardly convex form at the base-end side thereof relative to the insertion direction.

11. The oxygen sensor as claimed in claim 6, wherein the second portion includes a sub-cut formed therein extending from the bottom of the cut toward the base-end side relative to the insertion direction.

12. The oxygen sensor as claimed in claim 1, wherein the attachment portion, as observed in cross section, includes parallel portions which are located opposite each other along the direction of gap formation.

13. The oxygen sensor as claimed in claim 1, wherein, at a contact portion between the attachment portion of the metallic terminal member and the inner wall surface of the hollow portion of the oxygen detection element, a radius of curvature of an outer circumferential surface of the attachment portion is smaller than that of the inner wall surface.

14. The oxygen sensor as claimed in claim 1, wherein, a counter-bore portion is formed in a rear-end opening portion of the hollow portion of the oxygen detection element in a diameter-expanded manner so as to receive the attachment portion, directly or indirectly via another member.

15. The oxygen sensor as claimed in claim 1, wherein a lower end of the metallic terminal member comprises a diameter reduction portion including a press portion and a cut portion opposite the press portion, the oxygen sensor further comprises a heating member inserted into the metallic terminal member, and the press portion pushes the heating member toward the cut portion to bring the heating member into contact with the inner wall surface of the hollow portion of the oxygen detection element.

16. The oxygen sensor as claimed in claim 15, wherein the heating member is laterally biased from a center axis of the hollow portion of the oxygen detection element to contact the inner wall surface of the hollow portion of the oxygen detection element along substantially the entire length of the heating member.

17. The oxygen sensor as claimed in claim 1, further comprising a heating member movably inserted into the metallic terminal member.

* * * * *